(12) United States Patent
Carron et al.

(10) Patent No.: US 7,403,281 B2
(45) Date of Patent: Jul. 22, 2008

(54) RAMAN SPECTROMETER

(75) Inventors: Keith T. Carron, Centennial, WY (US); Mark A. Watson, Laramie, WY (US); Shane A. Buller, Laramie, WY (US)

(73) Assignees: University of Wyoming, Laramie, WY (US); Delta Nu a division of CC Technology, Inc., Laramie, WY (US)

( * ) Notice: Subject to any disclaimer, the term of this patent is extended or adjusted under 35 U.S.C. 154(b) by 300 days.

(21) Appl. No.: 10/859,372

(22) Filed: Jun. 1, 2004

(65) Prior Publication Data

US 2005/0248758 A1 Nov. 10, 2005

Related U.S. Application Data

(60) Provisional application No. 60/568,895, filed on May 7, 2004.

(51) Int. Cl.
G01J 3/44 (2006.01)
(52) U.S. Cl. .................................................. 356/301
(58) Field of Classification Search ................. 356/301
See application file for complete search history.

(56) References Cited

U.S. PATENT DOCUMENTS

| | | | |
|---|---|---|---|
| 5,112,127 A | | 5/1992 | Carrabba et al. |
| 5,139,334 A | * | 8/1992 | Clarke .......................... 356/301 |
| 5,615,673 A | * | 4/1997 | Berger et al. ................. 600/326 |
| 5,689,333 A | * | 11/1997 | Batchelder et al. ........... 356/301 |
| 6,205,354 B1 | * | 3/2001 | Gellermann et al. ........ 600/477 |
| 6,281,971 B1 | | 8/2001 | Allen et al. |
| 6,351,306 B1 | * | 2/2002 | Tedesco et al. ............... 356/301 |
| 6,558,958 B1 | * | 5/2003 | Pilevar et al. ................ 436/518 |
| 6,583,873 B1 | * | 6/2003 | Goncharov et al. .......... 356/326 |
| 6,693,280 B2 | * | 2/2004 | Sting et al. ............. 250/339.07 |
| 7,072,028 B2 | * | 7/2006 | Powell et al. ................... 356/72 |
| 7,102,746 B2 | | 9/2006 | Zhao |
| 2003/0053048 A1 | * | 3/2003 | Bennett et al. ............... 356/301 |
| 2005/0128476 A1 | * | 6/2005 | Zhao ........................... 356/301 |

OTHER PUBLICATIONS

Lewis, E. Neil; Treado, Patrick J.; and Levin, Ira W., A Miniaturized, No-Moving-Parts Raman Spectrometer, Applied Spectroscopy, Feb. 5, 1993, 5 pages, vol. 47, No. 5, Copyright 1993 Society for Applied Spectroscopy.

(Continued)

*Primary Examiner*—Tarifur Chowdhury
*Assistant Examiner*—Isiaka O Akanbi
(74) *Attorney, Agent, or Firm*—Hensley Kim & Holzer, LLC

(57) ABSTRACT

A system, method and apparatus for taking a Raman spectrum of a sample is disclosed. In one embodiment, for example, an integrated Raman spectrometer is provided. In another embodiment, a portable Raman spectrometer is provided. In another embodiment, a Raman spectrometer is provided comprising a collimated beam tube for transmitting excitation radiation to an external optical system, such as a microscope, a telescope or a camera lens. In another embodiment, a method for correcting a Raman spectrum for background interference is provided. In yet another embodiment, a method for rejecting fluorescence in a Raman spectrometer is provided. A chemical reactor comprising a built-in Raman detector for monitoring a chemical reaction in a reaction chamber of the reactor is also provided.

70 Claims, 22 Drawing Sheets

OTHER PUBLICATIONS

Cullum, Brian M.; Mobley, Joel; Chi, Zhenhuan; Stokes, David L.; Miller, Gordon H.; and Vo-Dinh, Tuan, Development of a Compact, Handheld Raman Instrument With No Moving Parts For Use in Field Analysis, American Institute of Physics, Review of Scientific Instruments, Apr. 2000, vol. 71, No. 4, American Institute of Physics Publishing, Melville, New York.

* cited by examiner

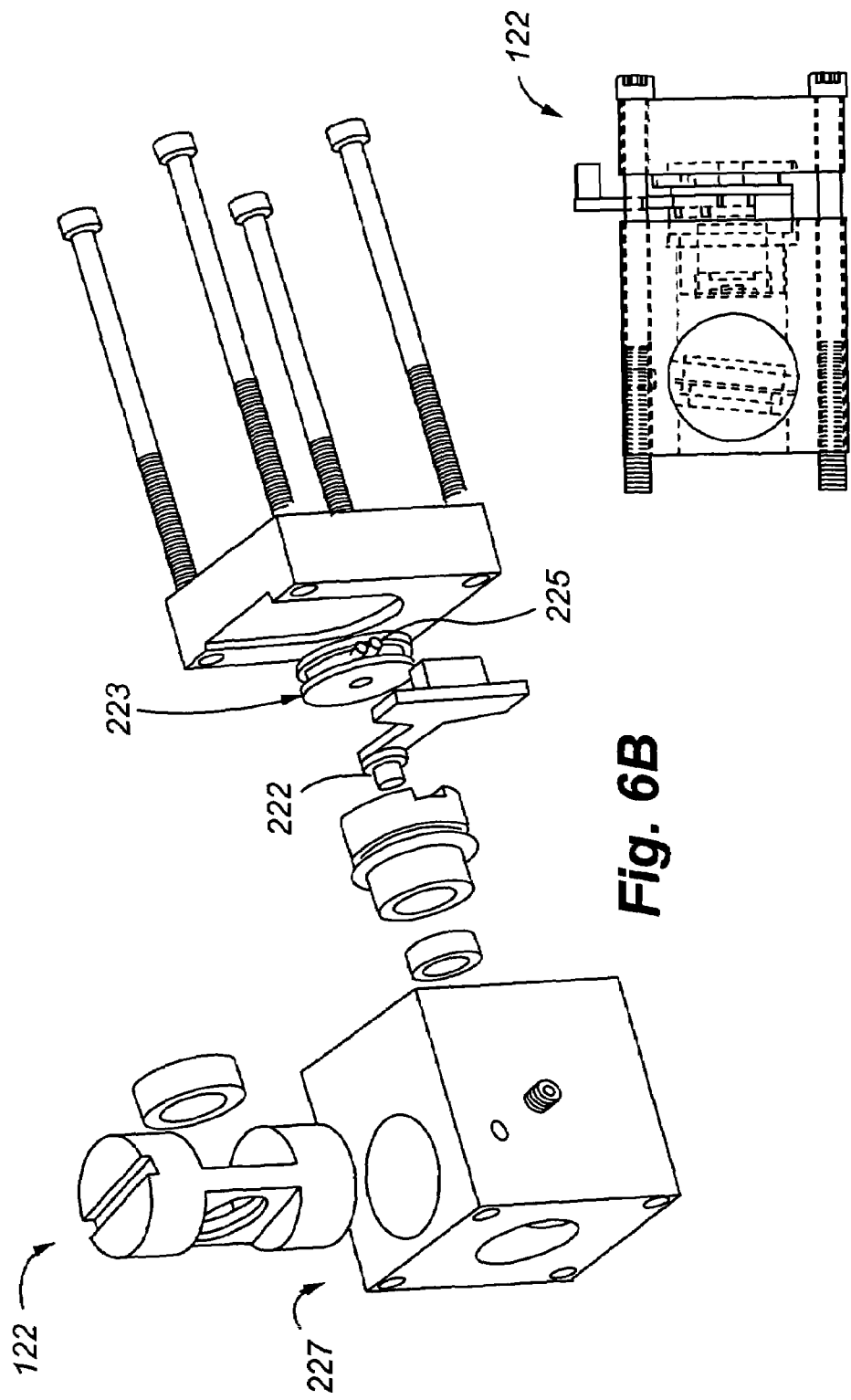

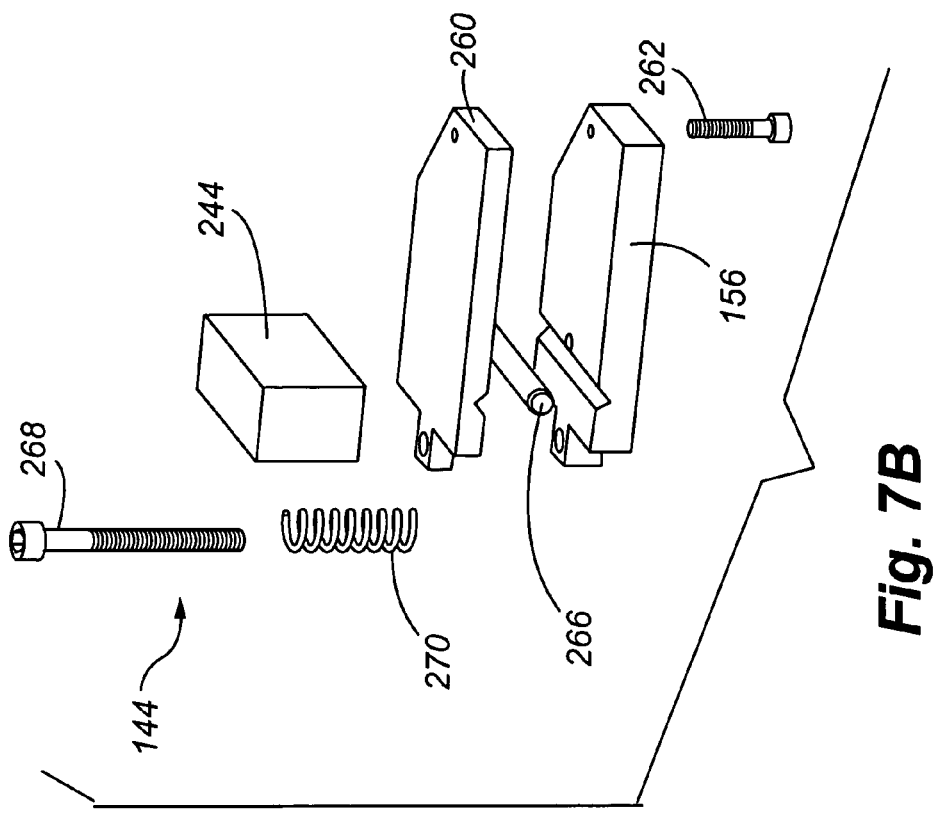
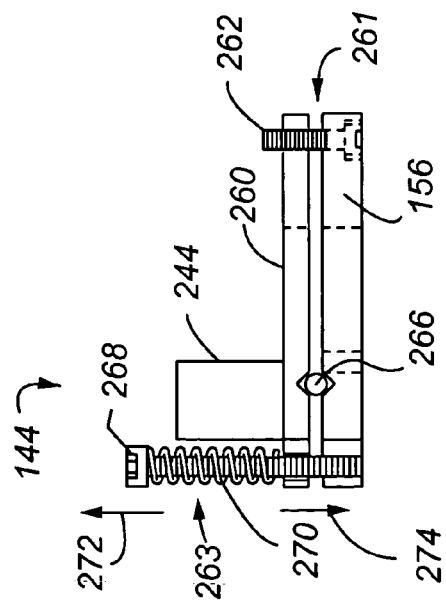
Fig. 7B
Fig. 7A

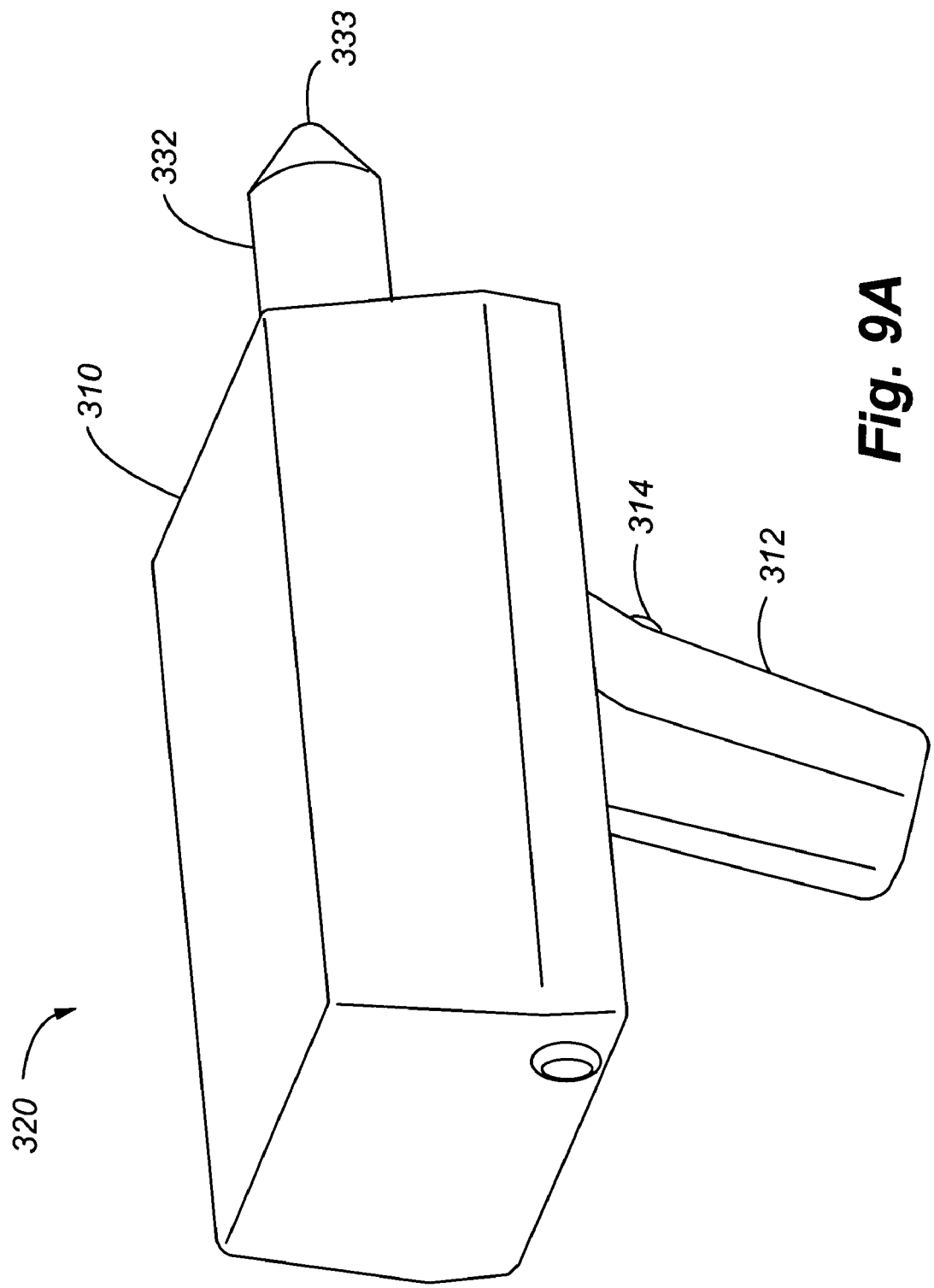

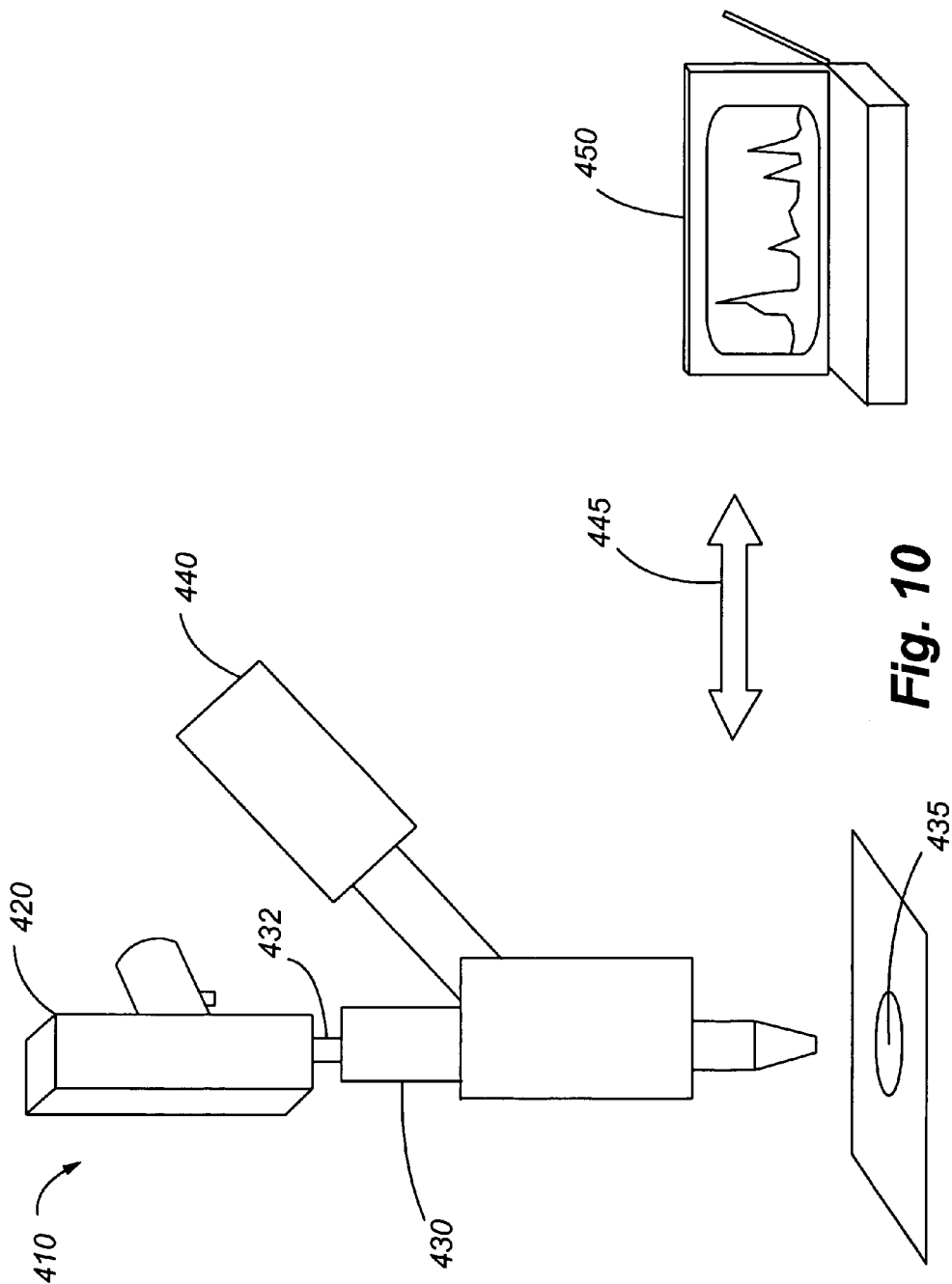

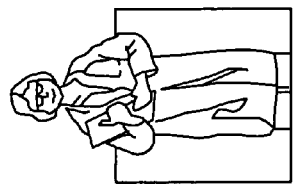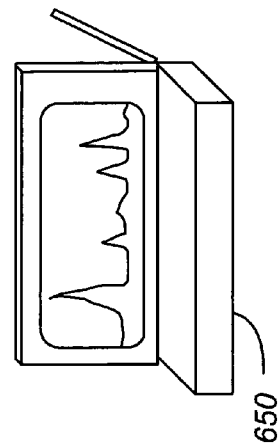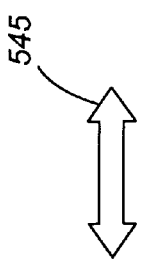
Fig. 11
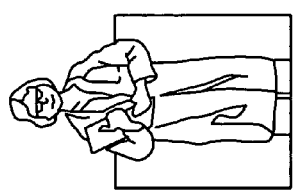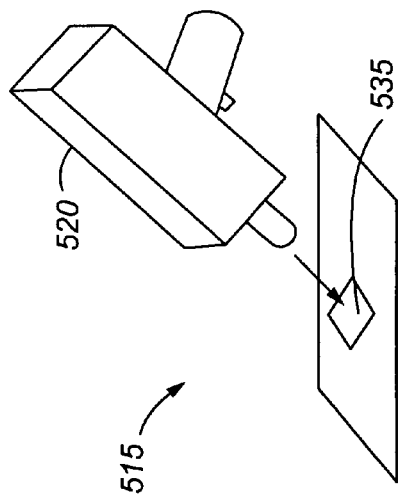

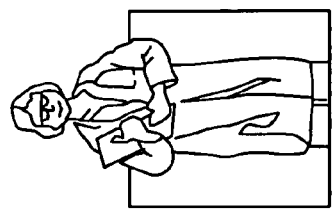
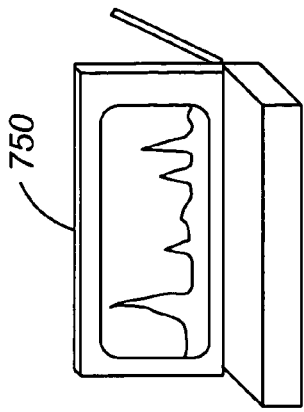
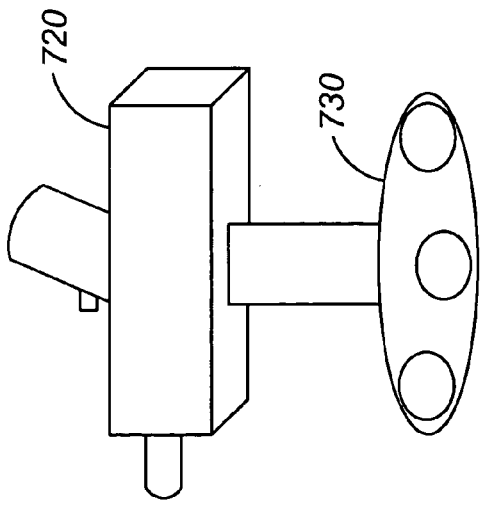
Fig. 13

RAMAN SPECTROMETER

CROSS-REFERENCE TO RELATED APPLICATIONS

The present application claims the benefit of U.S. Provisional Patent Application Ser. No. 60/568,895 entitled "Raman Spectrometer" and filed by Keith T. Carron et al. on May 7, 2004, which is incorporated into this application in its entirety.

STATEMENT REGARDING FEDERALLY SPONSORED RESEARCH OR DEVELOPMENT

This invention was made with Government support under Contract No. R44 DA13055 awarded by the National Institutes of Health. The Government has certain rights in this invention.

FIELD OF THE INVENTION

The present invention is generally related to the field of spectroscopy, and more particularly to a system, method and apparatus for adjusting spectral measurements to achieve a Raman spectrum.

BACKGROUND OF THE INVENTION

Spectroscopy is a general term for the process of measuring energy or intensity as a function of wavelength in a beam of light or radiation. Many conventional spectrometers, and components comprising a spectrometer system, also referred to as an instrument, may include basic features and components such as a slit and a collimator for producing a parallel beam of radiation, one or more prisms or gratings for dispersing radiation through differing angles of deviation based on wavelength, and apparatus for viewing dispersed radiation. Spectroscopy uses absorption, emission, or scattering of electromagnetic radiation by atoms, molecules or ions to qualitatively and quantitatively study physical properties and processes of matter.

Light or radiation directed at a target, or sample of physical matter, during operation of a spectrometer system may be referred to as incident radiation. Redirection of incident radiation following contact with a sample of physical matter ("sample") commonly is referred to as scattering of radiation. To the extent that atoms or molecules in a sample absorb all or a portion of incident radiation, rather than reflect incident radiation, a sample may become excited, and the energy level of the sample may be increased to a higher energy level. Electromagnetic radiation, including incident radiation, that passes through a sample, may produce a small portion of light that is scattered in a variety of directions. Light that is scattered but continues to have the same wavelength as the incident radiation will also have the same energy, a condition often referred to as Rayleigh or elastically scattered light. Incident radiation that is scattered during a change of vibrational state in molecules may be scattered with a different energy, and such scattered light may be called Raman scattered light. Such phenomena have been used in conjunction with spectroscopy to qualitatively and quantitatively study physical properties and processes, including identification of chemical properties, compositions, and structures of a sample.

A wave associated with electromagnetic radiation may be described by wavelength, the physical length of one complete oscillation, and by frequency of the wave, the number of oscillations per second that pass a point. If incident radiation is directed at a sample, the wavelength of the incident radiation may remain substantially unchanged in scattered radiation. Alternatively, if incident radiation is directed at a sample, the wavelength in the scattered radiation may acquire one or more different wavelengths than the incident wavelength. The energy differential between the incident radiation and the scattered radiation may be referred to as a Raman shift. Spectroscopic measurement of Raman scattered light seeks in part to measure the resulting wavelength of such scattered light.

Raman scattered light may occur at wavelengths shifted from the incident light by quanta of molecular vibrations. The phenomenon of Raman scattered light, therefore, is useful in spectroscopy applications for studying qualities and quantities of physical properties and processes, including identification of chemical properties, compositions, and structure in a sample. Currently, Raman shift spectroscopic analytical techniques are used for qualitative and quantitative studies of samples. If incident radiation is used to scatter light from a sample, and scattered radiation data is measured, the scattered radiation may provide one or more frequencies associated with the sample, as well as the intensities of those shifted frequencies. The frequencies may be used to identify the chemical composition of a sample. If, for example, intensities are plotted on a Y-axis, and frequency or frequencies are plotted on an X-axis, the frequency or frequencies may be expressed as a wave number, the reciprocal of the wavelength expressed in centimeters. The X-axis, showing frequency or frequencies, may be converted to a Raman shift in wave numbers, the measure of the difference between the observed wave number position of spectral bands, and the wave number of radiation appearing in the incident radiation.

While these principles and phenomena are known, until recently efforts to apply the principles and phenomena to qualitative and quantitative analyses of samples have not always resulted in uniform, predictable results, or in acceptable levels of precision and accuracy of Raman spectra. Because of instrumentation variabilities, inherent weakness of a Raman scattered signal, fluorescence, and other limitations associated with spectroscopy instruments, the goal of producing a standard Raman spectrum for use in sample analyses was, until recently, a challenge not achieved by apparatus and methods known in the art.

At least one problem that had to be overcome was the fact that spectroscopic measurements of Raman scattered light seeking to measure wavelength or intensities, or both, of scattered light, could be affected by the instrument, or spectroscopic system, itself. A number of components of an instrument may contribute individually and collectively to undesirable instrumentation variabilities that affect spectral data measured by the instrument. Raman scattered radiation from a sample may be observed, measured, and directed through an instrument by optics of a spectrometer, may be coded by a device such as an interferometer, and may be directed to one or more detectors to record Raman spectra. Any one, or all, of such components of a conventional spectrometer system induced or contributed to instrumentation variabilities that reduced or adversely affected the precision and accuracy of measurements of Raman scattered light.

In addition to fluorescence, spectral measurements of a source of incident radiation such as a laser, including semiconductor or diode lasers, will evidence other varying baseline components, artifactual or real, that preferably could be eliminated, suppressed, or compensated for to provide an accurate Raman spectrum for analytical purposes. In instrumentation designs preferred by users of Raman technology, semiconductor diode lasers would be the choice of incident radiation due to small and compact sizing, low heat dissipation, and high energy conversion efficiency. Use of semiconductor or diode lasers, while useful because of a number of important characteristics, also engender unique problems that, if solved, would advance Raman technology. However, at least one other problem associated with semiconductor diode lasers is the tendency for the output to change from one frequency to another during operation, commonly referred to as frequency drift. Frequency drift is generally related to temperature variations that may cause either slow frequency drifts or drastic frequency changes. Semiconductor diode lasers also are susceptible to mode hops when the laser switches output from one frequency to a new preferred frequency.

Some of the problems associated with frequency shifts were discussed as early as 1991 in Semiconductor Diode Lasers Volume I, edited by William Streifer and Michael Ettenberg, IEEE Press (1991), a work incorporated by reference into this document. In general, frequency shifts, or mode hops, are inherent in laser light, and can be eliminated only by redesigning the laser at excessive cost. Solutions for overcoming the effects of frequency shifts have included redesign of the internal cavity of lasers, designing what is known as an external cavity for lasers, and tuning a range of modes into a single mode. All of those solutions are achieved at considerable expense, and generally shorten the useful life of a semiconductor laser.

A further problem related to diode lasers includes variations in output intensity that directly affect the measured Raman shift. Rather than eliminate the problem physically, which is expensive and limits the effective life of the laser, it would also be useful to compensate for the frequency shifts and intensity variabilities. Thus, it is at least an objective of the present invention to overcome problems associated with using excitation sources in the visible range of light, including, for example, removal of fluorescence and other common mode noise from acquired spectra. U.S. Pat. No. 6,281,971 issued to Allen et al., for example, attempts to solve problems related to frequency drift in semiconductor or diode lasers. The '971 patent, however, requires monitoring the laser output frequency and performing complex integration routines to obtain a Raman spectrum for a sample.

Raman scattering is a comparatively weak effect when compared with Rayleigh or elastic scattering. Nevertheless, Raman scattering offers a significant opportunity for qualitative and quantitative studies of physical properties and processes, including identification of chemical compositions and structure in samples of physical matter. To appreciate these phenomena, as well as understand the problems solved by the present invention, it should be noted that depending on the compound comprising a sample, only about one scattered photon in $10^{6-8}$ tends to be Raman shifted. Because Raman scattering, therefore, is such a comparatively weak phenomenon, an instrument used to disperse radiation for measurement purposes should have minimal stray light and be able to substantially reject Rayleigh scattering; otherwise, a Raman shift may not be measurable.

As earlier described, Raman phenomena result in spectral information that is shifted relative to the excitation source, or source of incident radiation. Thus, any variations in the excitation source will result in a relative change, or shift, in spectral information. Spectrally shifted Raman information also is directly related to the intensity of the excitation source. A further complication arises from multiple lines in the frequency of the source of incident radiation that may cause shifted, multiple sets of spectra from a sample. Therefore, conventional Raman experimentation discloses that a source or sources of incident radiation that causes or cause excitation in a sample used in connection with a spectrograph should be substantially monochromatic, preferably providing a single frequency or wavelength. Recognition that the source of incident radiation requires a substantially monochromatic frequency has led to use of a variety of laser light sources as a source of incident radiation because of the substantially monochromatic frequency and high intensity of a laser. Gas lasers such as helium-neon, helium-cadmium, argon-ion, krypton-ion, as well as solid state lasers including Nd-YAG, and diode lasers, solid state tunable lasers, liquid dye lasers, and other lasers, have been used.

An undesirable result of incident radiation on a sample occurs if a sample generates red shifted radiation as part of a radiation absorption process, a phenomenon commonly referred to as fluorescence. Fluorescence occurs when absorbed radiation is reduced in frequency by internal molecular processes and emitted as radiation that is closer to the red end of the visible light spectrum. Fluorescence sometimes may be strong enough in comparison with the Raman shift to swamp, or substantially eliminate, the weaker Raman signal. Fluorescence is a major interference for samples using excitation wavelengths in the visible region of the light spectrum, and has therefore made use of blue and green excitation sources problematic. Using excitation sources in the far end of the red end of the light spectrum mitigates the fluorescence effect, however, particularly in connection with silicon detectors, but substantially restricts use of instrument components that tend to provide radiation far into the infrared ("IR") region of the light spectrum.

SUMMARY OF THE INVENTION

In one embodiment of the present invention, a spectrometer is provided for obtaining Raman spectrum information from a sample. The spectrometer comprises: a light source for providing an excitation radiation; a detector for detecting Raman scattered light; and an optical system for directing the excitation radiation toward the sample, receiving Raman scattered light from the sample and providing the Raman scattered light to the detector. The optical system of the spectrometer comprises a collimated beam tube for transmitting the excitation radiation in the form of a collimated light signal to an external optical system. In one embodiment, the collimated beam tube comprises a quartz material, such as a quartz tube. In another embodiment, for example, the collimated beam tube comprises a releasably engageable output module.

In one embodiment of the invention, a system comprising the spectrometer further comprises an external optical system. The external optical system, for example, comprises a microscope, a telescope and/or a camera lens.

In another embodiment of the present invention, an integrated spectrometer for obtaining Raman spectrum information from a sample is provided. The spectrometer comprises: a plate having a mounting surface; a light source module mounted to the mounting surface of the plate; a detector module mounted to the mounting surface of the plate; and an optical system mounted to the surface of the plate. The optical system of the integrated spectrometer is adapted to direct excitation radiation from the light source module to the sample, receive Raman scattered light from the sample, and provide the Raman scattered light to the detector module. In one embodiment of the integrated spectrometer, for example, the plate comprises a base plate. Further, in one particular embodiment, the integrated spectrometer comprises control electronics mounted on a single board that is mounted to the plate.

In one embodiment of an integrated spectrometer of the present invention, the optical system of the spectrometer comprises an adjustable diffraction grating for dividing the Raman scattered light into spatial separated wavelengths and for directing the spatial separated wavelengths toward the detector module. In one embodiment, for example, the adjustable diffraction grating comprises a diffraction surface fixed to a rocker. The rocker may further be adjustable to target the spatial separated wavelengths vertically at the detector module.

In another embodiment of the present invention, a method for correcting a Raman spectrum for background interference is provided. The method comprises providing a Raman spectrometer comprising: a light source for providing an excitation radiation; a detector for detecting Raman scattered light; and an optical system for directing the excitation radiation to the sample, receiving Raman scattered light from the sample, and providing the Raman scattered light to the detector. The method further comprises blocking the excitation radiation prior to the excitation radiation reaching the sample and reading the detector to obtain a background correction signal.

The excitation radiation may be blocked in a variety of manners and may be blocked at various locations of the spectrometer. In one embodiment, for example, the excitation radiation is blocked by shutting off the light source. In another embodiment, the excitation radiation is blocked via a shutter. Shutting off the light source and/or engaging a shutter may be accomplished manually by a user and/or may be electronically controlled by a controller of the spectrometer.

In another embodiment of the present invention, a portable spectrometer for obtaining Raman spectrum information is provided. The portable spectrometer comprises: a housing comprising a handle and an activation switch; a light source mounted within the housing for providing an excitation radiation; a detector mounted within the housing for detecting Raman scattered light; and an optical system for directing the excitation radiation to the sample external to the housing, receiving Raman scattered light from the sample, and providing the Raman scattered light to the detector. In one embodiment, the optical system comprises an output module attached to the housing for directing the excitation radiation to the sample and for receiving the Raman scattered light from the sample. The output module, in one particular embodiment, is releasably attachable to the housing. The output module, in another embodiment comprises a lens that focuses the excitation radiation at a terminal end of the output module.

A method and apparatus for rejecting fluorescence in a Raman spectrometer is also disclosed. In one embodiment, for example, a Raman spectrometer comprises: a laser light source for providing an excitation radiation; a detector for detecting Raman scattered light; and an optical system for directing the excitation radiation to a sample, receiving Raman scattered light from a sample and providing Raman scattered light to the detector. The temperature of the laser light source is controlled at a first predetermined temperature and Raman spectrum information is measured with the laser light source at about the first predetermined temperature to generate a first sampling signal. The temperature of the laser light source is also controlled to a second predetermined temperature after the measurement is taken at about the first predetermined temperature. Raman spectrum information is also measured with the laser light source at about the second predetermined temperature to generate a second sampling signal. A Raman feature signal is then generated by determining a difference between the first and second sampling signals.

In another embodiment, a chemical reactor is provided with a built-in Raman spectrometer for monitoring a chemical reaction. The chemical reactor comprises a reaction chamber for providing a chemical reaction and a Raman spectrometer built-in to the reactor for monitoring a chemical reaction in the reaction chamber. The Raman spectrometer comprises: a light source for providing an excitation radiation; a detector for detecting Raman scattered light; and an optical system for directing the excitation radiation toward the reaction chamber, receiving Raman scattered light from the reaction chamber and providing the Raman scattered light to the detector. In one embodiment of the chemical reactor, the Raman spectrometer monitors an amount of a product formed in the reaction chamber. In another embodiment, the reactor indicates that a reaction is complete based upon the amount of the product formed in the reaction chamber.

BRIEF DESCRIPTION OF THE DRAWINGS

FIG. 6A shows an assembled view of an embodiment of a light source module that may be used in the embodiment of an integrated Raman spectrometer of FIG. 5;

FIG. 6B shows an exploded view of the embodiment of a light source module shown in FIG. 6A;

FIG. 7A shows a side view of an assembled adjustable diffraction grating that may be used in the embodiment of an integrated Raman spectrometer of FIG. 5;

FIG. 7B shows an exploded view of the embodiment of an adjustable diffraction grating shown in FIG. 7A;

FIGS. 9A through 9D show various views of an embodiment of a portable Raman spectrometer of the present invention;

FIG. 10 shows a diagram of an embodiment of a portable Raman spectrometer for use in a system including an external optical system such as a microscope;

FIG. 11 shows a diagram of an embodiment of an embodiment of a system for remote Raman analysis comprising an embodiment of a portable Raman spectrometer;

FIG. 13 shows a diagram of an embodiment of an embodiment of a system for remote Raman analysis comprising an embodiment of a portable Raman spectrometer and a robot;

DETAILED DESCRIPTION

Figure 1:
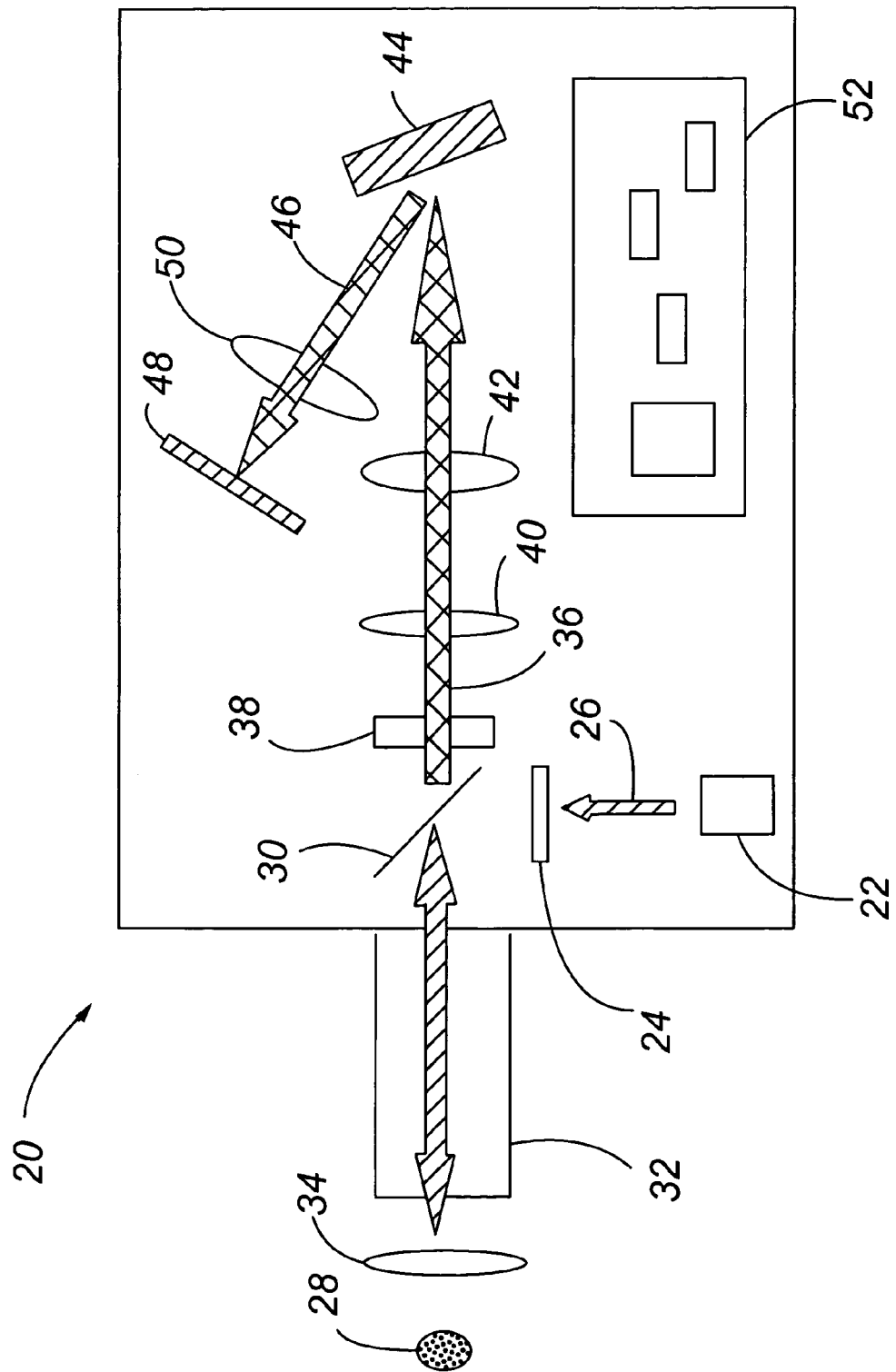
FIG. 1 shows an embodiment of a Raman spectrometer that may be utilized within the scope of the present invention.

FIG. 1 shows one embodiment of a Raman spectrometer 20 according to the present invention. As shown in FIG. 1, the Raman spectrometer comprises an excitation source 22. The excitation source 22 typically comprises a laser light source. In one embodiment, for example, the excitation source 22 comprises a diode laser. A diode laser, for example, is capable of providing a plurality of wavelengths from the excitation source 22. The spectrometer 20 further comprises a filter 24. The filter 24 filters the output of the excitation source 22, such as removing spurious emissions from the excitation source 22.

The spectrometer 20 further comprises a means for directing the incident beam 26 toward a sample 28. In the embodiment shown in FIG. 1, for example, the means for directing the incident beam 26 toward the sample 28 comprises a dichroic beam-splitter mirror 30. However, the incident beam 26 may be directed at sample 28 without any intervening instrument components being located in the path of incident beam 26. The incident beam 26 also may be directed at a mirror, a holographic transmissive element, a mirror formed with a hole in the mirror or any other means for directing an incident beam known in the art.

The spectrometer 20 optionally further comprises a collimated beam tube 32. In one embodiment, for example, the collimated beam tube 32, for example, may comprise a tube or length of free space through which the incident beam 26 and collected Raman scattered light is collimated. In this embodiment, neither the incident beam nor the collected Raman scattered light undergoes a change in size (e.g., focusing). The collimated beam tube 32 may comprise a variable length (e.g., via an adjustable tube, interchangeable tubes or a plurality of tubes that may be connected together to form a variable length tube). In another embodiment, the collimated beam tube 32 may comprise a quartz tube. In this embodiment, the quartz is resistant to microwaves and may be extended into a microwave oven.

Alternatively, the spectrometer 20 may comprise a fiber optic waveguide to direct the incident beam 26 toward the sample 28 and the collected Raman scattered light from the sample 28. The use of collimated light, however, provides benefits over non-collimated light such as that in a fiber optic waveguide. Losses associated with collimated light, for example, are significantly lower than those associated with non-collimated light. Thus, a collimated light beam may travel over further distances than non-collimated light and may be transmitted through a transparent solid without attenuating beyond a functional level.

The incident beam 26 may further be directed through a lens 34. In one embodiment, the lens 34 comprises a focusing lens in the path of the incident beam 26. The focusing lens couples the incident beam 26 with the sample 28 and collects the Raman scattered light from the sample. In another embodiment of the present invention, more than one lens 34 may be located in the path of the incident beam 26 before the incident beam 26 contacts the sample 28.

The incident beam 26 induces or generates on contact with the sample 28 scattered radiation having an energy differential different from, and one or more wavelengths different than, the incident radiation 26, or the Raman shift that, for convenience, is described in this document as a Raman beam 26. As stated above, and as shown in FIG. 1, in one embodiment the spectrometer 20 comprises a beam-splitter, such as a dichroic beam-splitter mirror 30. The Raman beam 36 is directed back through the lens 34 and the dichroic beam-splitter mirror 30 in a 180 degree back-scatter geometry. Neither the incident beam 26 nor Raman beam 36 need be co-linear. In the embodiment shown in FIG. 1, however, the Raman beam 36 passes back through the dichroic beam-splitter mirror 30 and then through a filter element 38. In one embodiment, the filter element 38 comprises a long pass filter that removes extraneous radiation (e.g., from the light source 22 or another source) prior to dispersing the Raman beam 36 into a spectrum. Alternatively, the filter element 38 may comprise a notch filter, or any other filter that is capable of rejecting elastically scattered radiation.

The Raman beam 36 may further pass through an input focusing lens 40 that focuses the Raman beam 36 to a point. In one embodiment, for example, an aperture or slit is located at the focal point of the input focusing lens 40. The aperture, slit or notch spatially filters the beam at the focal point of the input focusing lens.

The spectrometer 20 shown in FIG. 1 further comprises a collimating lens 42 that collimates the diverging Raman beam 36 after it has passed through the spatial filter aperture or slit. The collimating lens 42 further directs the re-collimated Raman beam toward a diffraction grating 44. The diffraction grating 44 comprises an optical element that divides the Raman beam into spatial separated wavelengths. The diffraction grating 44 further directs the divided Raman beam 46 toward a detector 48. The divided Raman beam 46 passes through a detector focusing lens 50 that focuses the spatially separated wavelengths of the divided Raman beam 46 onto the detector 48.

The detector 48 comprises a transducer that converts optical energy into an electrical signal. In one embodiment, for example, the detector 48 comprises an array of individual transducers that create an electrical pattern representing the spatially separated wavelengths of the Raman spectrum. A charge-coupled device (CCD) array, for example, may be used as the detector 48 in one embodiment of the invention. In another embodiment, an Indium-Gallium-Arsenide (In-GaAs) photodiode array detector may be used as the detector 48. Other detectors known in the art may also be used within a spectrometer of the present invention.

The spectrometer 20 further comprises control electronics 52 for controlling the operation of the spectrometer 20. The control electronics 52, for example, may control the operation of the light source 22, the detector 48, temperature control elements (e.g., for the light source or detector), and data transfer to and/or from the spectrometer. In one embodiment, the control electronics 52 may be integrated onto a single PC board within a housing of the spectrometer. The control electronics 52 may also comprise one or more discrete component(s) and/or one or more integrated circuit component(s).

In one embodiment, the control electronics 52 may comprise a means for communicating with an external device. The means for communicating, for example, the means form communicating may comprise a wired or wireless communication port for communicating with an external computer, personal data assistant (PDA), network or the like. A wired communication port, for example, may comprise a parallel, serial, universal serial bus (USB), FireWire™, IEEE 1394, Ethernet, modem, cable modem or other wired communication port known in the art. A wireless communication port, for example, may comprise an antenna for wireless communicating with an external device, such as via and infrared, Bluetooth, IEEE 802.11a/b/g, IrDA, a wireless modem or other wireless communication port known in the art. The control electronics 52 may be powered from a battery for a portable device or may include a power input for receiving power from an external supply as known in the art. A battery or power supply circuit (e.g., a rectifier) may be located within a housing of the spectrometer 20.

The Raman spectrometer 20 of FIG. 1 operates to detect a Raman spectrum of a sample 28. In order to detect the Raman spectrum, the light source 22 is activated to generate an incident beam 26 of excitation radiation, such as generating a laser incident beam in a laser light source. In one embodiment, for example, the temperature of the light source 22 is controlled to control the output frequency of the incident beam 26 generated by the light source 22. The incident beam 26 of excitation radiation passes through the filter 24, which removes spurious emissions from the incident beam. The incident beam is next reflected off the beam-splitter mirror 30 toward the sample 28. The incident beam 26 travels through the collimated beam tube 32 and is focused onto the sample 28 by the output focusing lens 34.

The incident beam generates Raman scattered light from the sample 28. The Raman scattered light is collimated by the output focusing lens 34 and transmitted back through the collimated beam tube 32 to the beam-splitter mirror 30. In this embodiment, the beam-splitter mirror 30 passes the Raman scattered light through the mirror 30 to the filter 38. From the filter 38, the Raman scattered light passes through the input focusing lens 40 and is focused onto a spatial filter such as an aperture, slit or notch. The Raman scattered light is spatially filtered and diverges toward the collimating lens 42. The collimating lens 42 collimates the diverging Raman scattered light and transmits the light to the diffraction grating 44, which divides the Raman scattered light into spatial separated wavelengths and directs the wavelengths towards the detector element 48. The spatially separated wavelengths of the Raman scattered light pass through the detector focusing lens 50 and are focused into a focused band of radiation that represents the spatially separated wavelengths of the Raman scattered light. The focused band of radiation is further directed by the detector focusing lens 50 onto the detector 48. The detector 48 comprises an array of individual transducers that each generate an electrical signal corresponding to intensity of the radiation received at each of the individual transducers. The electrical signals generated at the individual transducers of the detector represents the spatially separated wavelengths of the Raman spectrum of the sample 28. The electrical signals are read from the detector by the control electronics 52. In one embodiment, for example, the spectrometer 20 may then present the Raman spectrum detected to a user such as via a display or indicator on the spectrometer itself. In another embodiment, the control electronics of the spectrometer 20 may comprise a look-up table stored in a data storage element (e.g., memory, tape or disk drive, memory stick or the like). In this embodiment, the control electronics 52 compares the signal from the detector with the values stored in the look-up table to determine a result of the Raman scan. The spectrometer 20 then presents the result to a user such as via a display or indicator on the spectrometer. The result, for example, may indicate the presence or absence of one or more chemicals or substances in the sample and may further indicate an amount or concentration of a chemical or substance detected by the spectrometer.

Background Correction

In one embodiment of a spectrometer 20 of the invention, the spectrometer 20 detects ambient conditions at the detector 48 by shutting off the light source 22 (e.g., laser) or otherwise blocking the excitation radiation generated by the light source from reaching the detector. In this embodiment, for example, the light source 22 may be shut off under the control of the control electronics 52 or under the control of a user prior to taking a Raman scan of a sample. Alternatively, the excitation radiation generated by the light source 22 may be blocked from the detector such as through the use of a shutter or other blocking mechanism. The shutter or other blocking mechanism block the excitation radiation from reaching the detector 48 at various locations within the spectrometer 20. In one embodiment, for example, the excitation radiation may be blocked before the excitation radiation reaches the optical system of the spectrometer 20 (e.g., adjacent to the light source 22). In another embodiment, the excitation radiation may be blocked within the optical system of the spectrometer 20 but at a location that allows ambient light to reach the detector (e.g., between the filter 24 and the beam-splitter 30). In a further embodiment, the excitation radiation may be blocked within the optical system of the spectrometer 20 at a location that may also impact the amount of ambient light that reaches the detector. For example, a shutter located between the beam-splitter 30 and the filter 38 would block ambient light entering the spectrometer 20 through the optical system at the collimated beam tube 32 or the output focusing lens 34 but may still allow some ambient light entering the spectrometer from another location to reach the detector 48. As described above, the shutter or blocking mechanism may be operated under the control of the control electronics 52 or under the control of a user prior to taking a Raman scan of a sample.

In one embodiment, at least most of the excitation radiation generated by the light source 22 is blocked prior to the excitation radiation reaching the sample. In another embodiment, at least about 90% of the excitation radiation is blocked prior to the excitation radiation reaching the sample. In yet another embodiment, substantially all of the excitation radiation generated by the light source 22 is blocked prior to reaching the sample.

When the light source of the spectrometer 20 is disabled or blocked, the detector 48 acquires background sources of light from outside the spectrometer 20 (e.g., from the output focusing lens) and from inside the spectrometer 20. The detector 48 further generates a background correction signal from the acquired background light. The background correction signal is then subtracted from the signal acquired during a Raman scan. The subtraction of the background correction signal removes background noise associated with ambient interferences and additionally noise associated with the detector itself.

Fluorescence Rejection

As described above, fluorescence occurs when absorbed radiation is lowered in frequency by internal molecular processes and emitted as radiation that is closer to the red end of the visible light spectrum. Fluorescence sometimes may be strong enough in comparison with the Raman shift to swamp, or substantially eliminate, the weaker Raman signal.

Figures 2A, 2B:
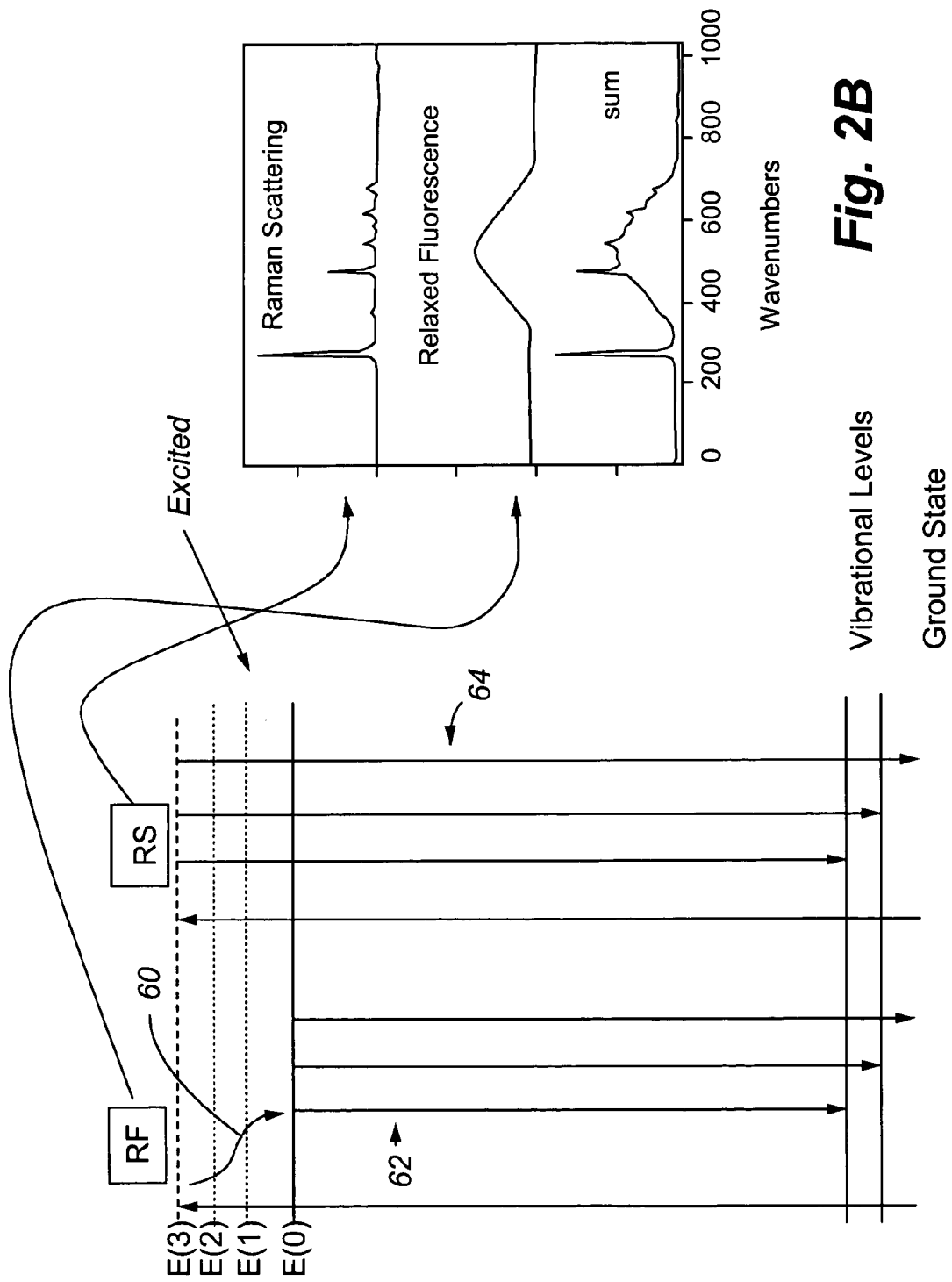
FIG. 2A shows a graphical depiction of (1) an optical process RF that leads to relaxed fluorescence in a sample illuminated by excitation radiation, and (2) an optical process RS associated with Raman scattering.
FIG. 2B shows a graphical representation of exemplary spectra for (a) a Raman scattering, (b) relaxed fluorescence, and (c) a combined measured spectra including a Raman scattering component and a relaxed fluorescence component.

FIG. 2A, for example, shows a graphical depictions of (1) an optical process RF that leads to relaxed fluorescence in a sample illuminated by excitation radiation, and (2) an optical process RS associated with Raman scattering. As shown in FIG. 2A, both optical processes, RF and RS, begin with the sample being excited to a first excited state E(3) due to the illumination of the sample with excitation radiation. Relaxed fluorescence, shown in the process RF, is characterized by vibrational relaxation 60 of the excited state induced in the sample from a first induced excited state E(3) to the lowest vibrational level in the excited state E(0). Then, from the lowest vibrational level in the excited state E(0), an emission process 62 occurs from the lowest vibrational level in the excited state E(0).

Raman scattering, however, is characterized by instantaneous emission 64 from the first excited state E(3) instead of first undergoing a relaxation to a lower excited state. As shown in FIG. 2B, these processes are shown as distinct Raman features in the case of Raman scattering RS and a relatively featureless band in the case of relaxed fluorescence RF. Since both processes occur simultaneously, the observed Raman spectrum comprises the sum of the Raman scattering spectrum and the relaxed fluorescence spectrum as shown in FIG. 2B.

Further, as shown in FIG. 2B, the relaxed fluorescence peaks at frequency levels such as in the range from about 450 nm to 650 nm, while decreasing at frequencies in the near-infrared and infrared range. In one embodiment of the present invention, a near infrared (e.g., a 785 nm diode laser) or an infrared light source is used as the light source of a spectrometer 20 in order to minimize fluorescence caused by the light source.

Figures 3A, 3B:
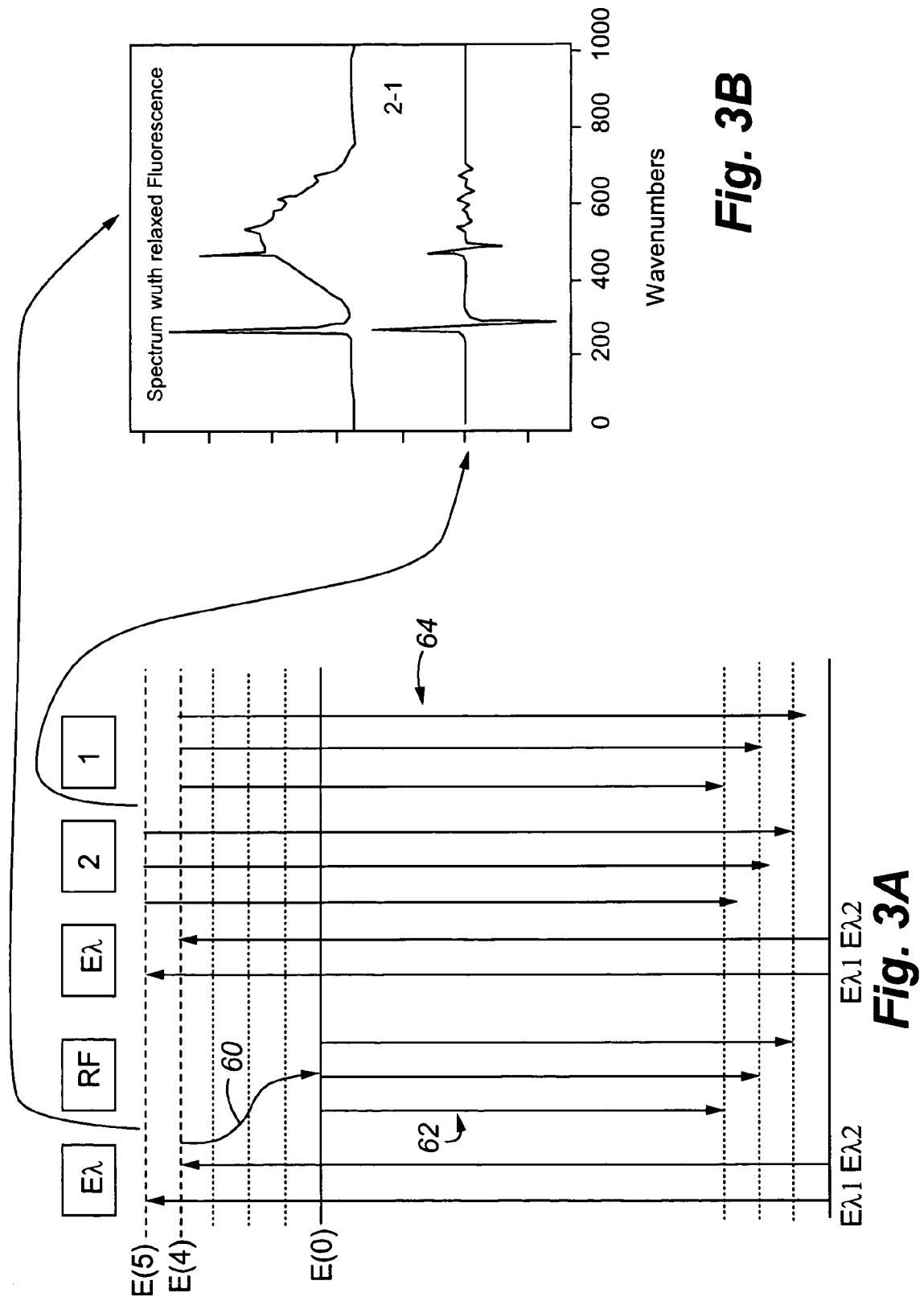
FIG. 3A shows a graphical depiction of (1) an optical process RF that leads to relaxed fluorescence in a sample illuminated by excitation radiation, and (2) an optical process RS associated with Raman scattering, wherein the excitation is accomplished by illuminating a sample by two different frequency excitation radiation sources.
FIG. 3B shows (a) a combined measured spectra including a Raman scattering component and a relaxed fluorescence component, and (b) a result of a method for rejecting fluorescence within the scope of the present invention.

FIGS. 3A and 3B show the result of an embodiment of a fluorescence rejection method for use in accordance with the present invention. In FIG. 3A, an optical process RF that leads to fluorescence and an optical process RS associated with Raman scattering are shown for excitation of the sample at two different frequencies Eλ1 and Eλ2 of excitation radiation. As shown in the relaxed fluorescence process RF, vibrational relaxation to the lowest excited state E(0) at both frequencies. Thus, when the two fluorescence spectra (following the illumination of the sample of each excitation frequency Eλ1 and Eλ2) are subtracted, the two fluorescence spectra cancel each other out and lead to a flat background of zero.

With Raman scattering, however, the instantaneous emission from the excited states E(4) and E(5) caused by illumination of the sample by wavelengths Eλ1 and Eλ2 result in Raman scattered wavelengths that are also shifted in wavelength. Thus, when the two different Raman spectra (following the illumination of the sample by each excitation frequency Eλ1 and Eλ2) are subtracted, the resulting waveform comprises both positive and negative peaks from the Raman spectra.

When a sample exhibits both relaxed fluorescence and Raman scattering, the subtraction of the two spectra obtained by illumination of the sample at each excitation frequency Eλ1 and Eλ2 results in a flat baseline centered around zero (as shown in FIG. 3B) and shows a spectrum comprised of both positive and negative Raman features. If the baseline is not centered around zero due to noise, an appropriate noise reduction scheme such as the background correction method described above or any other noise reduction scheme known in the art may be used to shift the baseline to zero or approximately zero. In one particular embodiment, for example, the negative or the positive Raman features may be discarded and the Raman spectrum may be determined by the positive or negative Raman features, respectively.

In one embodiment, a diode laser (such as a 785 nm diode laser) is used as the light source 22 of a spectrometer 20. Through various control methods, the output frequency of the diode laser may be controlled such that monitoring the laser wavelength is unnecessary. In one embodiment, for example, the output frequency of a diode laser is controlled as described below by controlling the temperature of the diode laser. In one embodiment, for example, the laser temperature may be controlled by a thermoelectric module or other temperature control element. Because a diode laser often exhibits hysteresis, one embodiment of controlling the output frequency by controlling the temperature of the diode laser is to approach a diode laser temperature for taking a measurement of a Raman spectrum from the same direction each time. Thus, in this embodiment, when a Raman measurement is to be taken of a sample with a diode laser at a predetermined diode laser temperature, the predetermined temperature is approached from the same direction (either heating or cooling) each time a measurement is to be taken.

Figure 4:
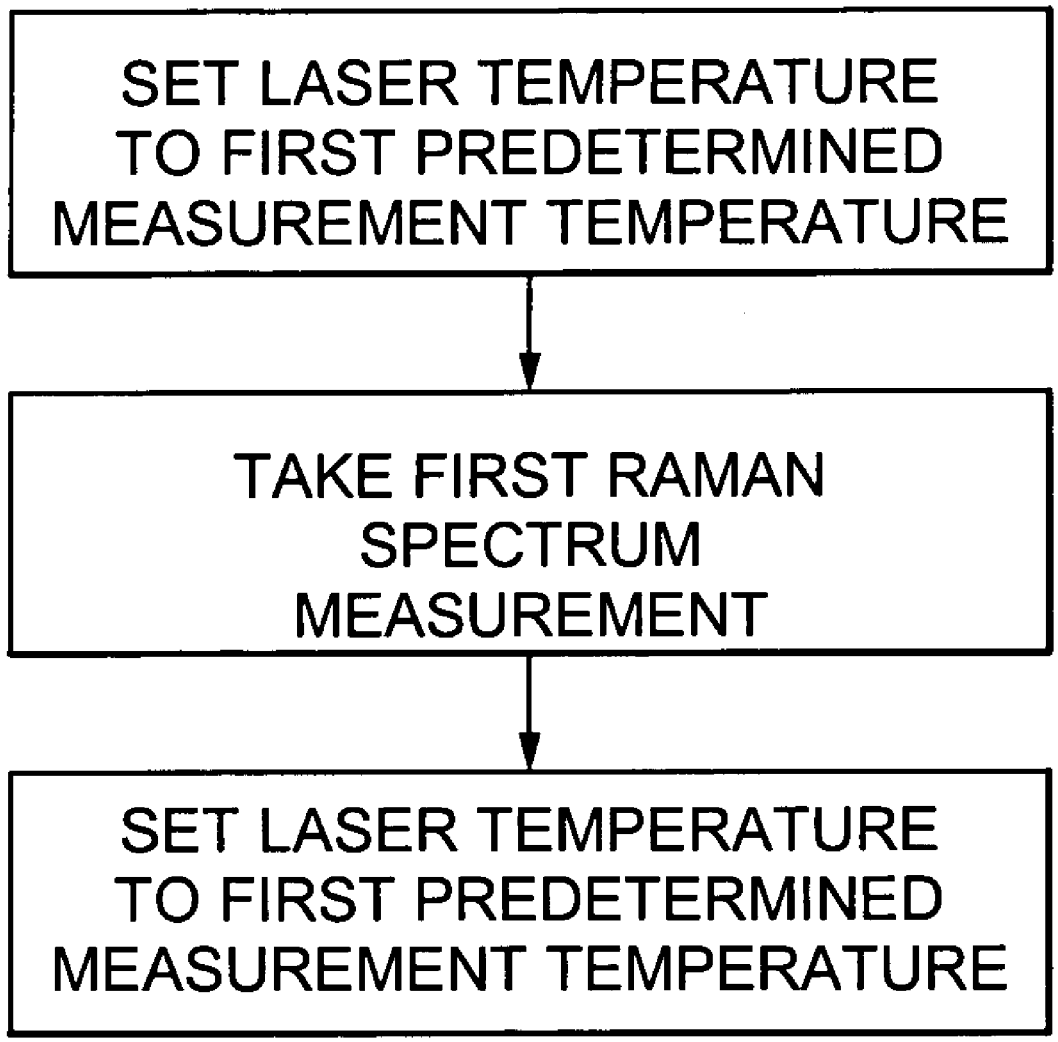
FIG. 4 shows a flow diagram of one embodiment of a method for measuring Raman scattered light that may be used in accordance with a method for rejecting fluorescence within the scope of the present invention.

A flow chart of an embodiment of a method 70 for controlling a diode laser to illuminate a sample at two different frequencies is shown in FIG. 4. In this embodiment, the laser is set at a first predetermined measurement temperature (e.g., 31° Celsius) in operation 72. In an embodiment of the invention, hysteresis of the diode laser may be avoided by first bringing the temperature of the diode laser to a temperature below or above the first predetermined measurement temperature so that the temperature of the diode laser approaches the first predetermined temperature from the same direction each time. For example, the diode laser may be cooled below the first predetermined measurement temperature or to a predetermined temperature lower than the first predetermined measurement temperature (e.g., 28° Celsius if the first predetermined measurement temperature comprises 31° Celsius) prior to setting the temperature of the diode laser at the first predetermined measurement temperature. The diode laser is then heated to the first predetermined measurement temperature. By starting at a first predetermined temperature and moving the same direction (up or down in temperature) each time a sample is to be illuminated, the output frequency of the diode laser is controlled.

Next, a first Raman spectrum of a sample is taken while the diode laser is at the first predetermined measurement temperature in operation 74. After the first Raman spectrum is taken in operation 74, the temperature of the diode laser is changed to a second predetermined measurement temperature (e.g., 34° Celsius) in operation 76. As described above, the second predetermined measurement temperature can be approached from the same direction each time in order to avoid hysteresis of the diode laser output frequency.

Figure 17:
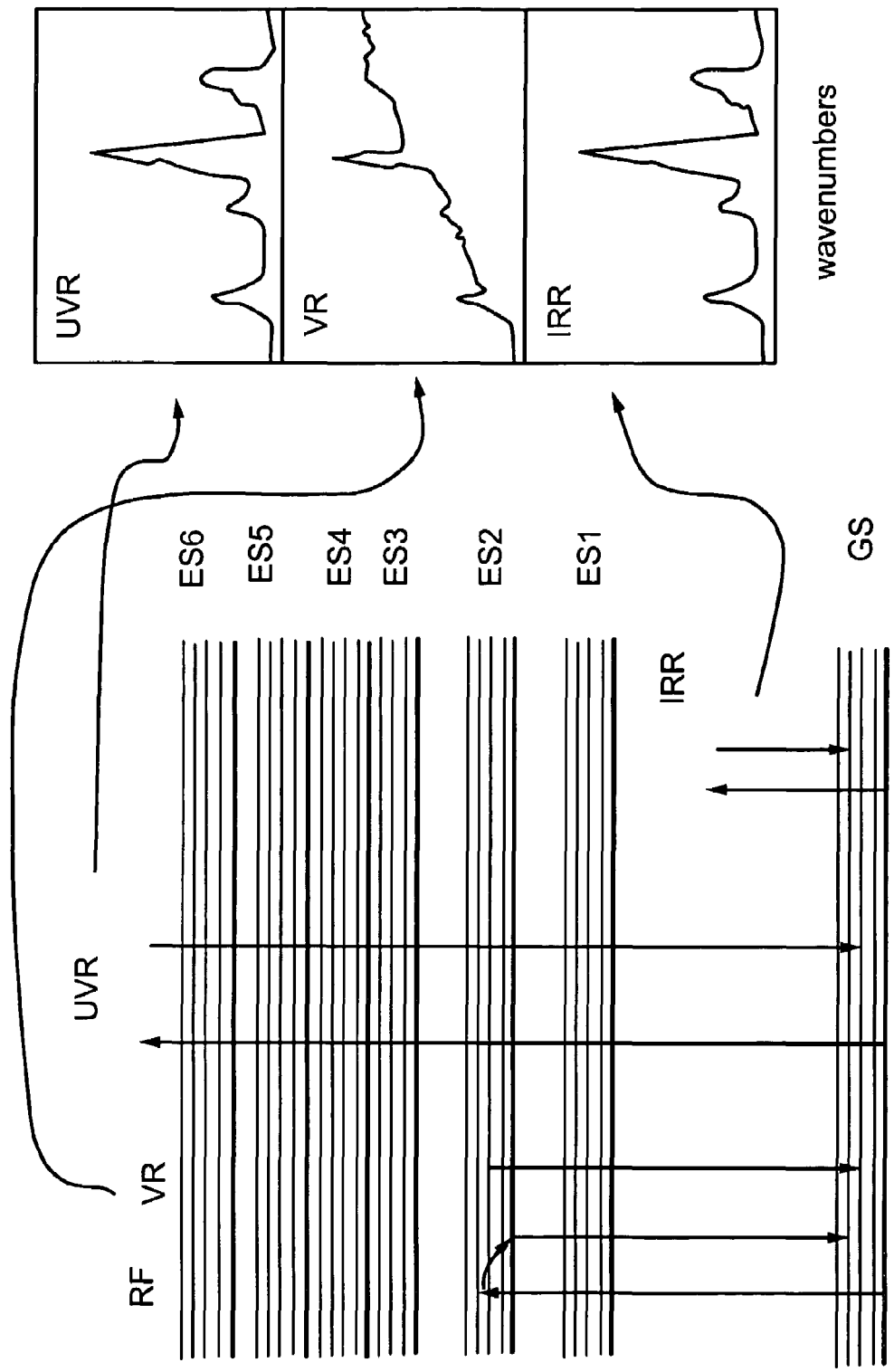
FIG. 17 shows an exemplary graphical depiction of Raman scattering and relaxed fluorescence for excitation radiation in ultraviolet radiation wavelengths, visible radiation wavelengths and infrared wavelengths.

FIG. 17 further shows that a pure sample comprising a single molecule (e.g., where the molecule itself fluoresces) or a sample comprising a molecule in a matrix (e.g., where the molecule itself and/or components of the matrix fluoresce) will contain multiple excited electron states (ES). With visible laser excitation, both visible Raman scattering (VSR) and relaxed fluorescence (RF) can occur. To avoid fluorescence, the frequency of the excitation laser may be shifted as shown in FIG. 17. For example, the frequency of the excitation laser may be shifted so that the laser energy is far above the excited electron states (e.g., ultraviolet radiation (UVR)). Alternatively, the frequency of the excitation laser may be shifted so that the laser excitation is located below any of the excited electron states (e.g., infrared radiation (IRR)).

A UV laser required to excite a molecule or sample is very complex, costly and physically large. It is not compatible with small, low-cost Raman spectrometers. Likewise, current IRR systems use the principle of Fourier Transform spectroscopy to acquire a Raman spectrum. This has been traditionally performed because sensitive infrared detectors have not been available in Raman spectrometers. Since an infrared detector's inherent noise level was high it has been common to put the whole spectrum on the detector at once. This is the principle of Fourier Transform Raman spectroscopy. However, the interferometric method of obtaining a spectrum is very expensive, optically inefficient and is not robust.

In one embodiment of the present invention, however, an infrared diode laser (e.g., 980 nm) is used with a dispersive spectrometer. Minor changes, as one skilled in the art would recognize, are made to the filters and optics to accommodate the infrared laser diode. An embodiment of a spectrometer of the present invention including such an infrared diode laser will further comprise an Indium-Gallium-Arsenide (InGaAs) detector. Such detectors are used, for example, in night vision scopes and are very sensitive detectors at infrared wavelengths. In recent years, InGaAs detectors have been made with high efficiency, low noise and in an array format similar to a CCD. Array InGaAs detectors allow a spectrometer to function as described above and below with respect to a near infrared diode laser (e.g., 785 nm), but with significantly improved IR sensitivity. A dispersive spectrometer comprising an infrared excitation source and an InGaAs detector will further provide an inherently higher sensitivity than a near infrared or UV wavelength system.

Integrated Spectrometer

Figure 5:
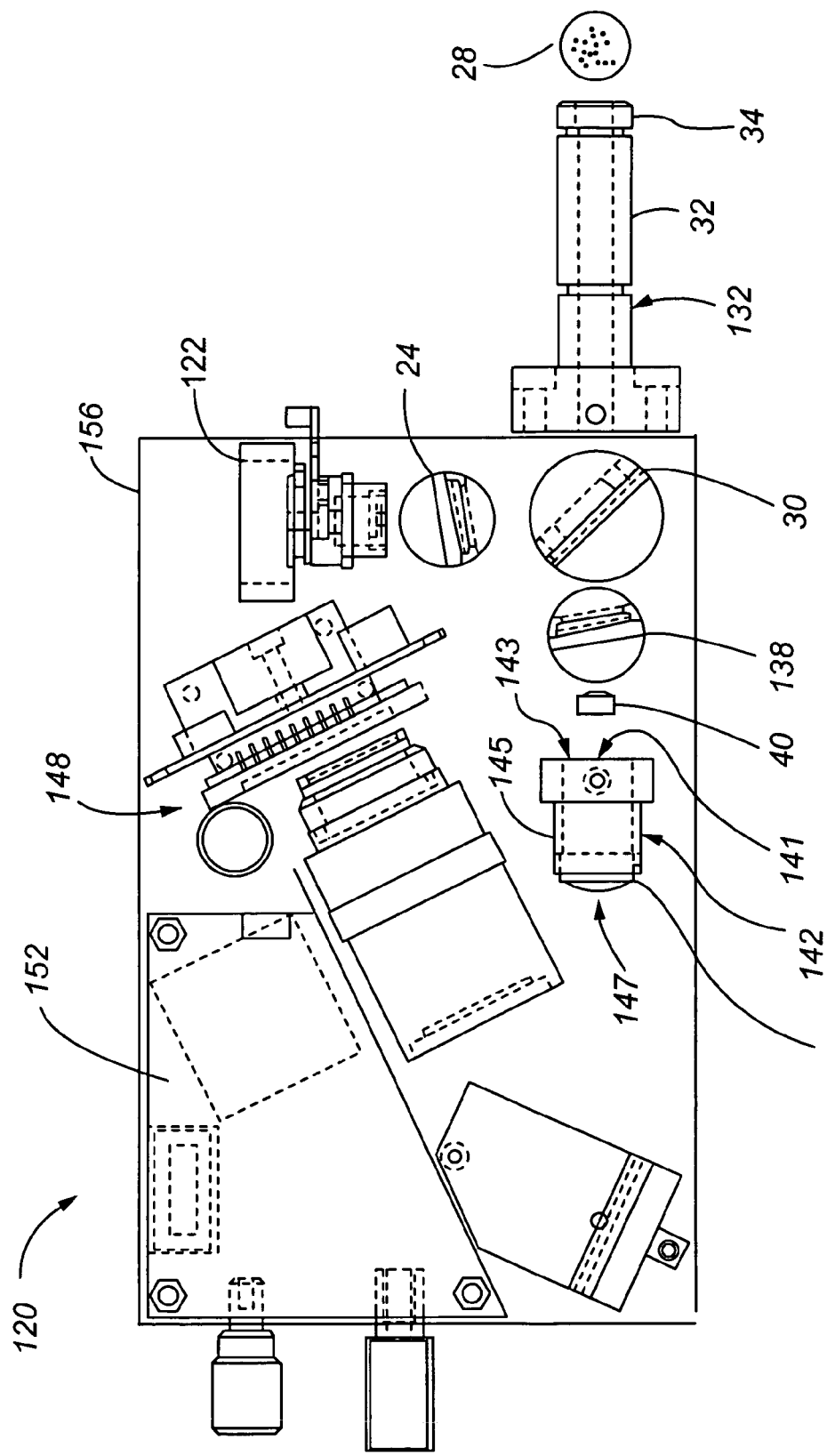
FIG. 5 shows a top plan view of one embodiment of an integrated Raman spectrometer within the scope of the present invention.

FIG. 5 shows an embodiment of an integrated spectrometer 120 according to the present invention. The integrated spectrometer 120 comprises components of the spectrometer integrated onto a single optical platform such as the baseplate 156 and, in one embodiment, further comprises the control electronics 152 for the excitation source 122 and the detector 148 located on a single circuit board. Where the elements are the same as described with reference to FIG. 1, the reference numbers remain the same and are not described in further detail.

The spectrometer 120 comprises a light source module 122 for generating an incident beam of excitation radiation and a filter 24, such as a 785 nm, 0.5 inch diameter laser cleanup filter for filtering the excitation radiation of the incident beam. An embodiment of the light source module 122 that may be used with a spectrometer in accordance with the present invention is shown in FIGS. 6A and 6B. FIG. 6A shows the light source module 122 assembled and FIG. 6B shows an exploded view of the light source module 122. In one embodiment, for example, the light source module 122 comprises a laser 222 for providing an incident beam. The laser may comprise any laser known in the art for use in a Raman spectrometer. In one embodiment, for example, the laser 222 comprises a laser diode, such as a 785 nm, 80 mW laser diode, a He Ne laser, or any other laser source known in the art.

The light source module 122 further comprises a temperature control element 223, such as a thermoelectric module or other temperature control elements known in the art. As described above, one problem associated with the use of a diode laser in the light source module 122 of the spectrometer 120 is the tendency for the output to exhibit frequency drift during operation depending on the temperature of the laser. Thus, by controlling the temperature of the laser, as described above, the frequency of the diode laser may be controlled. The thermoelectric module 223 comprises leads 225 through which the control electronics 152 control the temperature of the thermoelectric module 223. The light source module 122 further comprises a housing 227 fixing the laser 222 and the thermoelectric module 223 relative to each other and the housing is fixed within the spectrometer 122, such as to a base plate 156, to maintain the light source module 122 in the proper configuration for the optical system of the spectrometer 120.

The spectrometer 120 further comprises a beam-splitter mirror 30 for directing the incident beam of the excitation radiation toward a sample 28. In one embodiment, for example, the beam-splitter mirror 30 comprises a 797 nm, 0.55 mm×0.8 mm×1 mmm beam-splitter dichroic mirror.

An output module 132 of the spectrometer 120 further transmits the incident beam, focuses the incident beam onto the sample (or operates with an external optical system to focus the incident beam onto the sample as described below) and receives reflected Raman scattered light from the sample. In the embodiment shown in FIG. 5, for example, the output module comprises a collimated beam tube 32 and an output focusing lens 34. The collimated beam tube 32 comprises a tube 32 having an output focusing lens 34 mounted on one end of the tube 32. The output module 132 may be built into the spectrometer 120 or may be an interchangeable module that releasably mounts onto the spectrometer 120, such as to a housing of the spectrometer 120. Different shaped or length output modules, for example, may be used with the spectrometer depending upon the type of sample (e.g., solid, liquid or gas) or the location of the sample (e.g., within a reaction chamber). Further, as described in more detail below, the output module may not comprise the output focusing lens 34 if the spectrometer is to be used in combination with another optical system (e.g., a microscope or telescope). In this embodiment, the incident beam exits the collimated beam tube as collimated light and enters the other optical system. The collimated beam tube 32 further receives reflected Raman scattered light from the sample as collimated light from the other optical system.

The spectrometer 120 also comprises a long pass filter 138 that removes extraneous radiation (e.g., from the light source module 122 or another source) prior to dispersing the Raman beam into a spectrum. In one embodiment, for example, the long pass filter 138 comprises an HQ800, 0.5 inch diameter long pass filter, which is available from Chroma Technology Corporations in Rockingham, Vt.

The Raman beam is also passed through an input focusing lens 40. The input focusing lens 40, for example, comprises a 6.25 mm×10 mm MgF2 F45-208 lens achromat in one embodiment. The input focusing lens 40 focuses the Raman beam on an aperture 141 of a spatial filter module 142. The spatial filter module 142 comprises an aperture 141 formed in a surface of the spatial filter module 142. In one embodiment, for example, the aperture comprises a 100 micron aperture formed in an input portion 143 of the spatial filter module 142. The spatial filter module 142 further comprises a housing 145 connecting the input portion 143 containing the aperture 141 with a collimating lens 42 mounted on an output side 147 of the spatial filter module 142. The housing 145 of the spatial filter module 142 maintains the aperture 141 and the collimating lens 42 in a fixed orientation and at a fixed distance from each other. The collimating lens 42 collimates the diverging Raman scattered light received from the aperture 141 and directs the collimated light to the diffraction grating 44 of the spectrometer 120.

FIGS. 7A and 7B show an embodiment of an adjustable diffraction grating 144 that may be used with a spectrometer in accordance with the present invention. FIG. 7A shows the adjustable diffraction grating in an assembled configuration, and FIG. 7B shows an exploded view of the adjustable diffraction grating. The diffraction grating 144 is adjustable to vertically align the Raman beam onto the center of a detector element (e.g., a CCD array). As shown in FIG. 7B, the diffraction grating 144 comprises a diffraction surface 244 for dividing the scattered Raman beam into spatial separated wavelengths. The diffraction grating 144 further comprises a means for adjusting the diffraction surface 244.

In the embodiment shown in FIGS. 7A and 7B, for example, the means for adjusting the diffraction surface 244 comprises a rocker 260 to which the diffraction surface 244 is fixed, either directly or indirectly. The rocker surface 260 is fixed to the spectrometer 120 (e.g., to a housing, base plate 156 or the like) such as via fixed connector 261. In the embodiment shown in FIG. 7, for example, the fixed connector 261 comprises a fixed screw 262 that fixes the rocker 260. The rocker 260 is further connected to the spectrometer 120 (e.g., to a housing, base plate or the like) via an adjustable connector 263 at a location displaced from the fixed connector 261. The rocker 260 pivots about pin 266 in the embodiment shown in FIG. 7, for example, the adjustable connector 263 comprises a set screw 268 and biasing member 270 (e.g., a spring). The biasing member 270 biases the rocker in a first direction 272 and the set screw 268 allows for the adjustment of the rocker 260 in a second direction 274 opposite to the first direction 272 by tightening (or loosening) the set screw 268. In this manner, the set screw 268 may be adjusted to vertically align the Raman beam on a detector element.

Figure 8A:
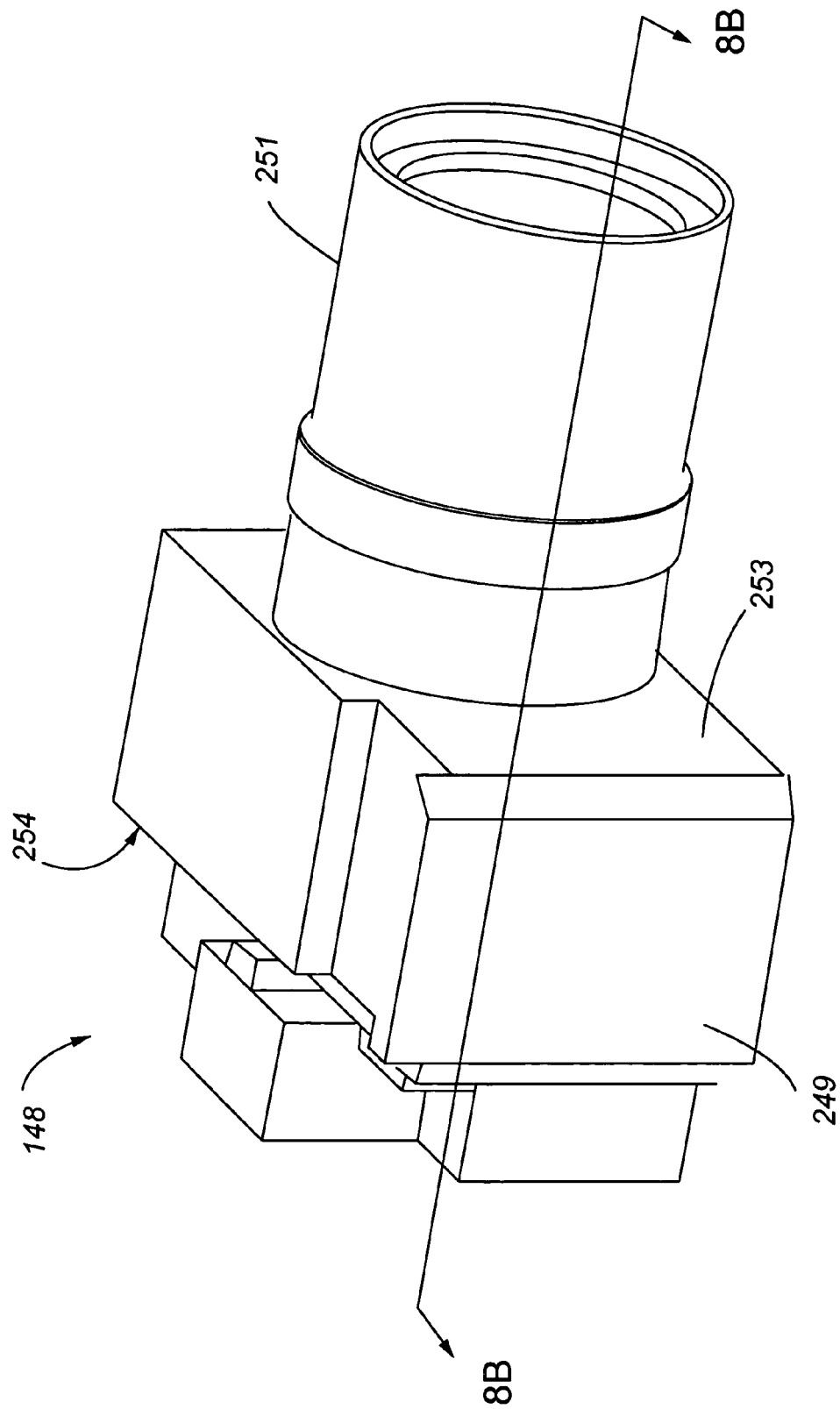
FIG. 8A shows a perspective view of an embodiment of an assembled detector module that may be used in the embodiment of an integrated Raman spectrometer of FIG. 5.
Figure 8B:
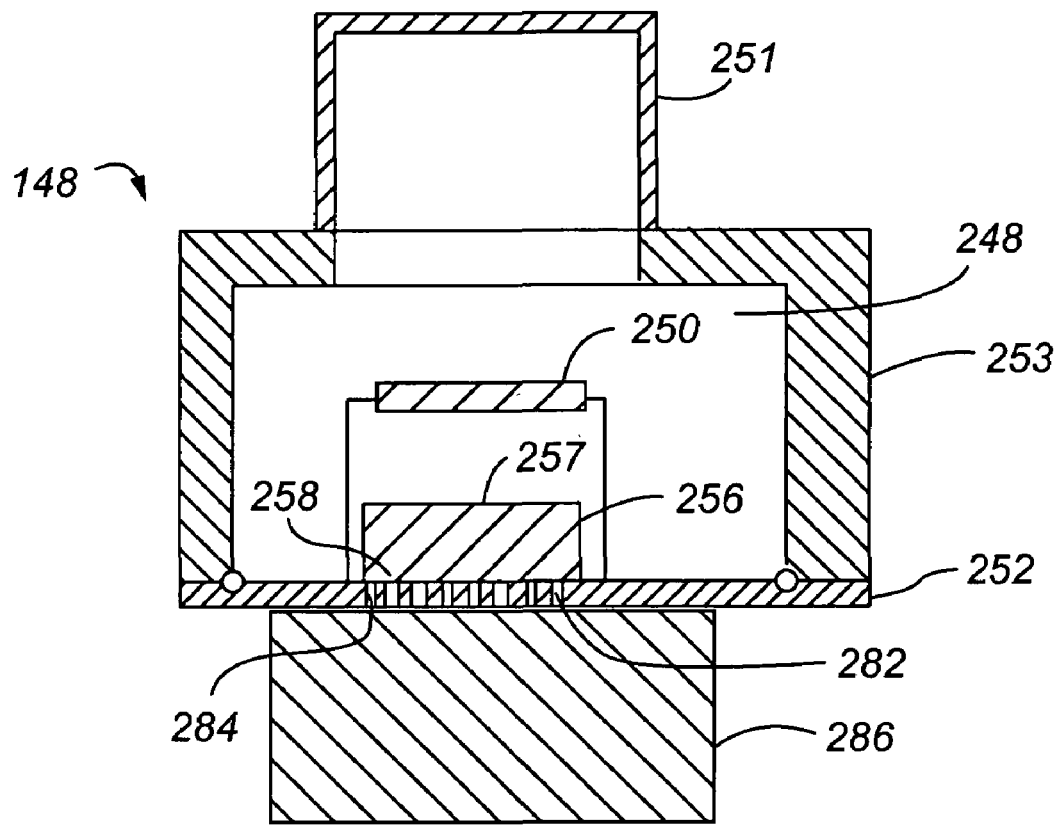
FIG. 8B shows a cross-sectional view of the embodiment of an assembled detector module shown in FIG. 8A taken along section line 8B-8B.
Figure 8C:
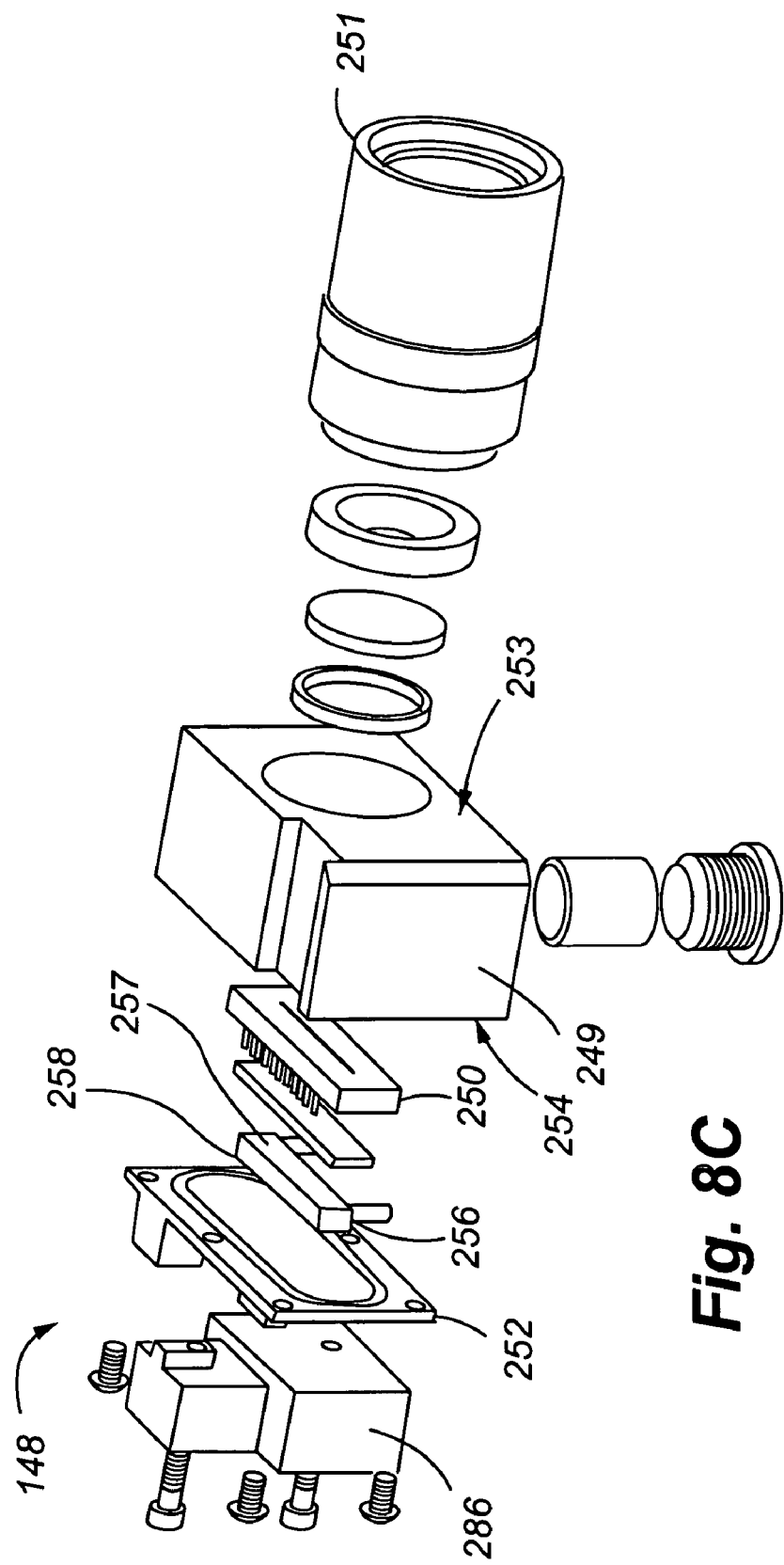
FIG. 8C shows an exploded view of the embodiment of an assembled detector module shown in FIG. 8A.
Figure 9B:
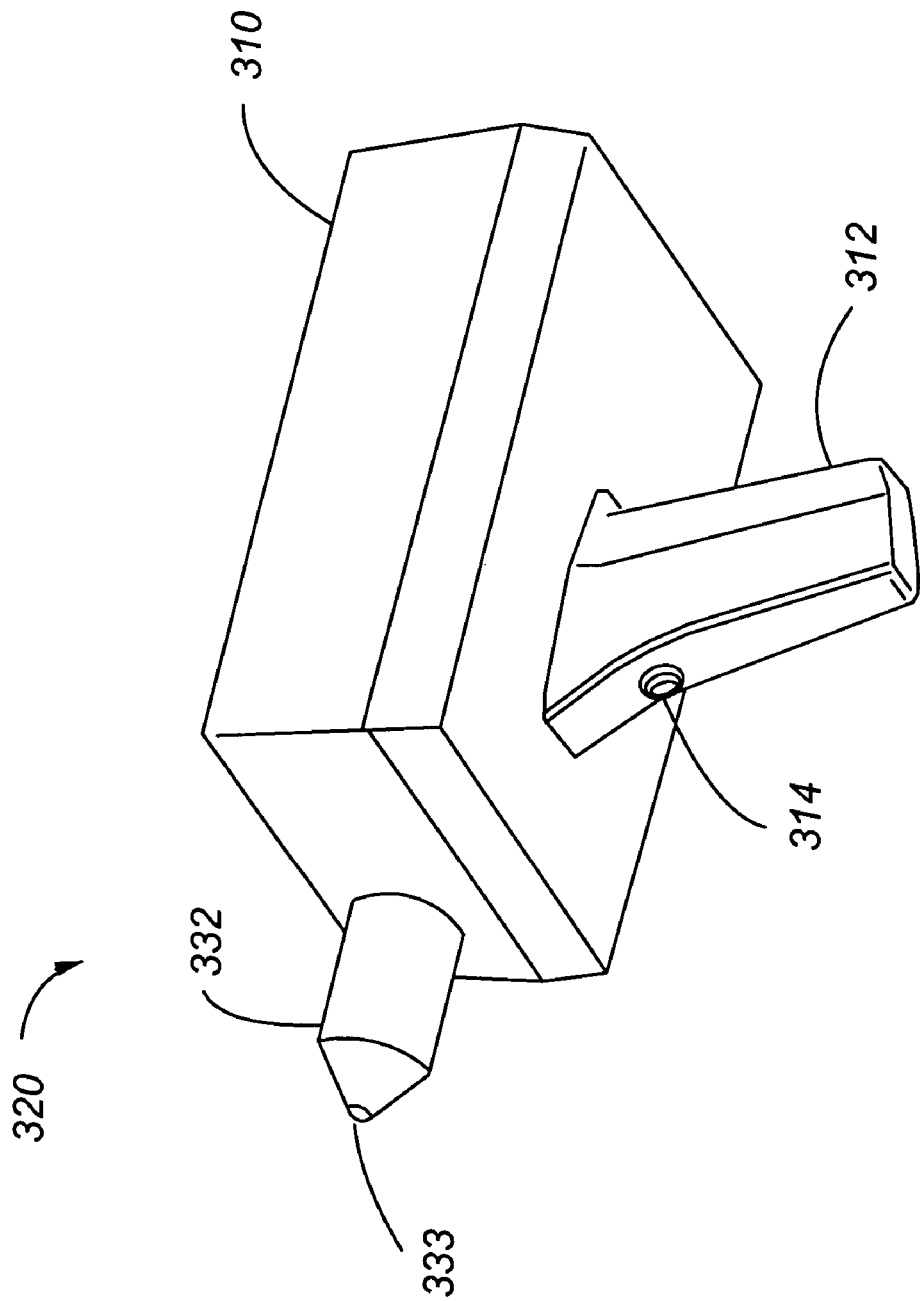
Figure 9C:
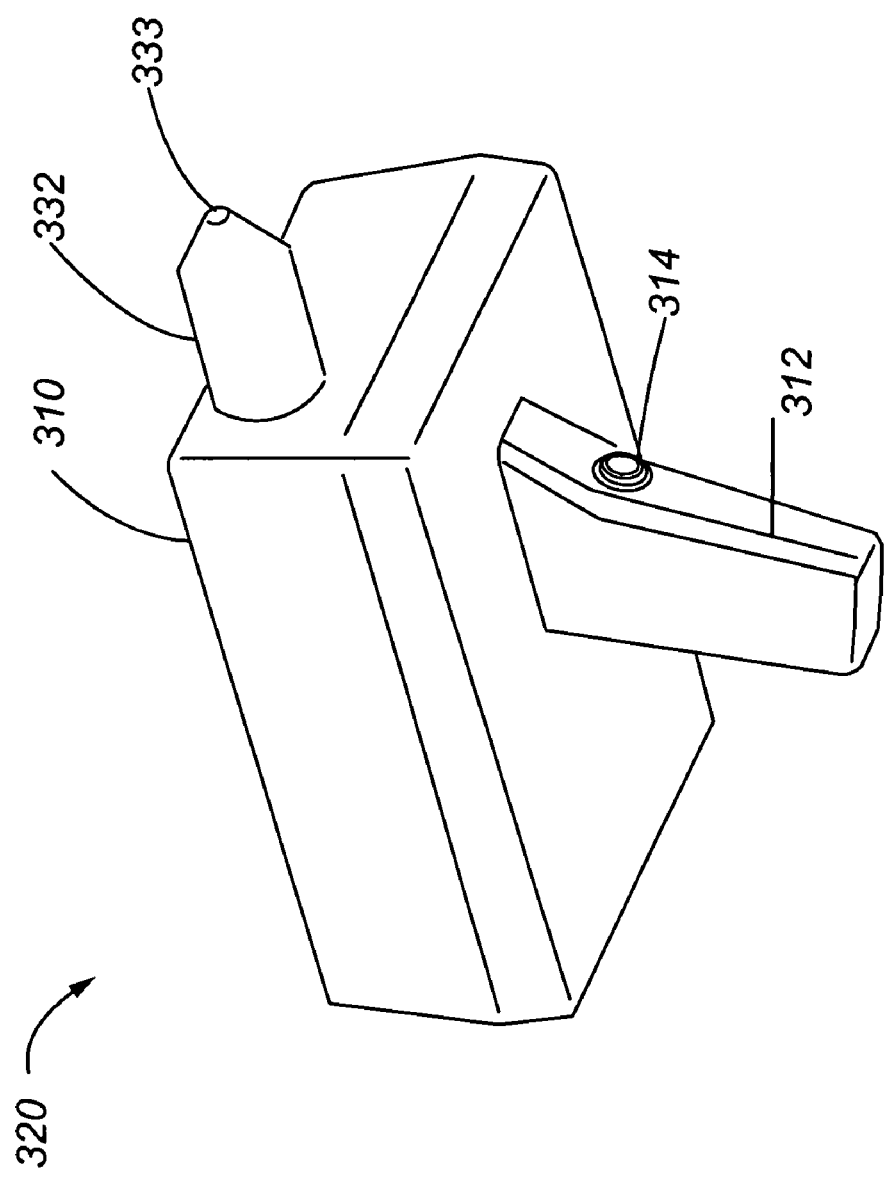
Figure 9D:
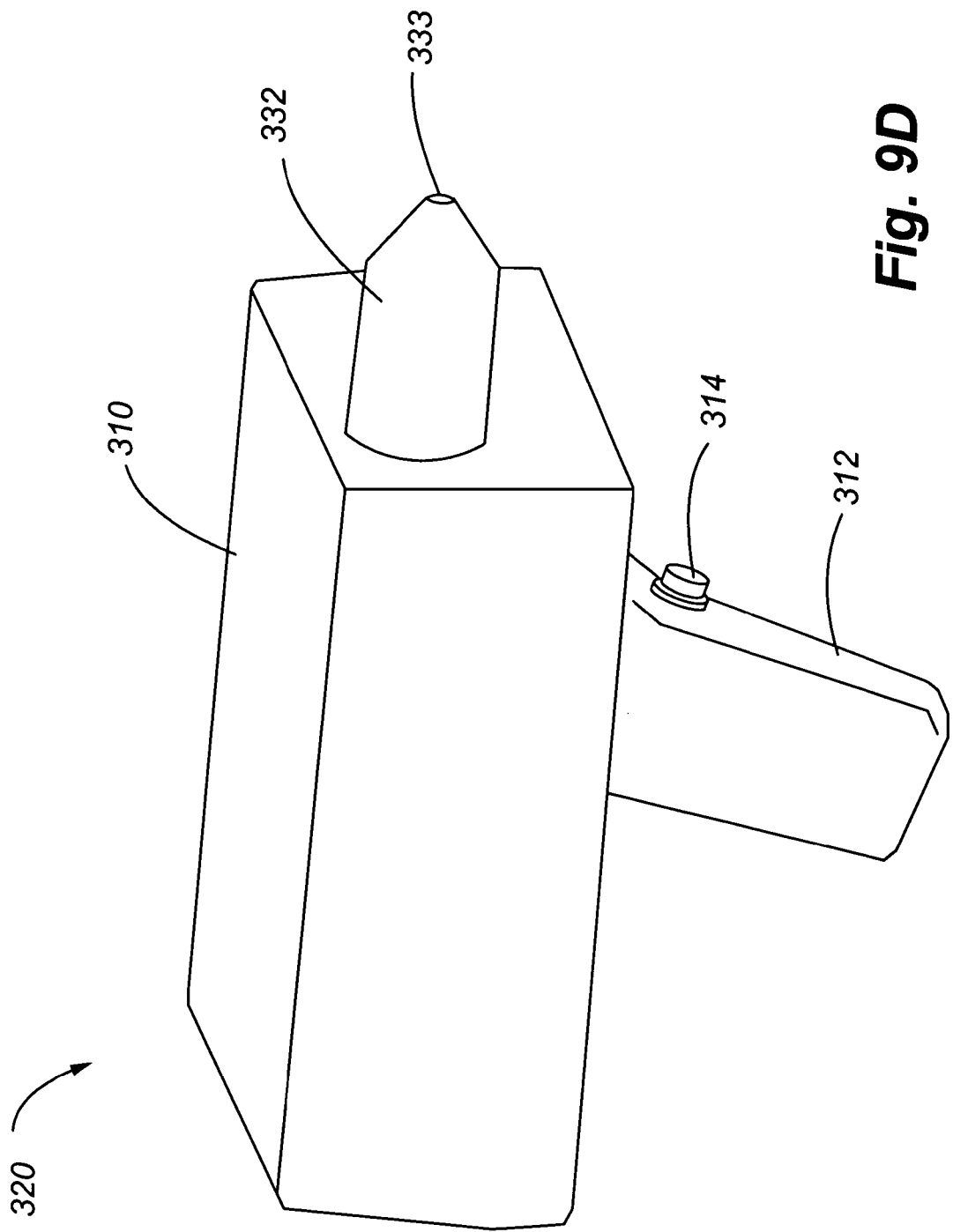

FIGS. 8A, 8B and 8C show a detector module 148 that may be used with a spectrometer 120 of the present invention. FIG. 8A shows the detector module 148 assembled, FIG. 8B shows a cross-sectional view of the detector module 148 and FIG. 8C shows an exploded view of the detector module 148. The detector chamber 248, in the embodiment shown in FIGS. 8A through 8C, comprises a sealed chamber 249 in which a CCD array detector element 250 is housed. The chamber 248 is formed of a housing 249, a detector focusing lens 251 and a PC board 252. The detector focusing lens 251 is mounted to a front portion 253 of the housing 249 for receiving the divided Raman beam from the diffraction grating 144 (shown in FIG. 5) and focusing the divided Raman beam on the CCD array detector element 250. The PC board 252 is mounted on a rear portion 254 of the housing 249 to enclose the chamber 248. The chamber 248 may be sealed at the front and rear portions 253 and 254 such as through the use of o-rings or other sealing means known in the art at the detector focusing lens 251 and the PC board 252, respectively.

The chamber 248 may further include a desiccant to remove moisture from the air within the chamber 248. In one embodiment, the detector module 148 may further comprise a humidity sensor and/or a temperature sensor for monitoring the humidity and/or temperature within the chamber 248. The humidity sensor and/or the temperature sensor may be monitored by the control electronics 152 of the spectrometer 120 (shown in FIG. 5). The control electronics 152 may monitor the humidity sensor to determine if the humidity in the chamber is within a predetermined range or above a predetermined threshold for acceptable operation of the spectrometer 120. If the humidity is above the predetermined threshold, for example, the control electronics 152 may inform a user of the spectrometer 120 that the desiccant in the chamber 248 should be replaced. The control electronics 152 may inform a user such as through a display or other indicator on the spectrometer 120 itself or may communicate with a user through a message sent to an external device such as a computer or PDA.

The CCD array detector element 250 is located within the detector chamber 248. The CCD array 250 is electrically connected to a PC board 252 via leads 255. The leads 255 are used to collect the charge information received by the individual transducers of the CCD array 250. The detector module 148 further comprises a thermoelectric module 256 used for controlling the temperature of the CCD array 250 and/or the temperature of the chamber 248. The thermoelectric module 256 comprises a "cool" side 257 and a "hot" side 258. The cool side 257 faces the CCD array 250 and receives heat energy from the CCD array 250 and transfers that heat to the hot side 258. As shown in the embodiment of FIG. 8B, the thermoelectric module 256 is mounted on the PC board 252. The hot side 258 of the thermoelectric module 256 is located adjacent to one or more heat conductive elements 280 of the PC board 252. In one embodiment, for example, the heat conductive elements 280 of the PC board are formed by vias 282 in the PC board 252. The vias 282 in the PC board 252 may comprise open vias or may be partially or completely filled with a heat conductive material 284, such as copper, conductive epoxy or solder. Where the chamber 248 is sealed to maintain a controlled environment for the CCD array detector element 250, the vias 282 may be filled or at least partially filled with the heat conductive material 284 to prevent an additional seal from being required to maintain the seal of the chamber 248 where a heat sink is extended through the PC board 252.

The detector module 148 further comprises a heat sink 286 for further transferring the heat energy captured by the thermoelectric module 256 away from the chamber 248. In the embodiment shown in FIG. 8B, for example, the heat sink 286 is located adjacent to the vias of the PC board 252. The heat energy transferred from the hot side 258 of the thermoelectric module 256 through the vias 282 is further transferred away from the chamber 248 by the heat sink 286. Where the vias 282 are filled (or at least partially filled) with a heat conductive material 284, the seal of the chamber 248 may be maintained without as many penetrations into the chamber 248 that provide potential locations for leaks in the seal.

FIGS. 9A through 9D show various views one embodiment of a portable Raman spectrometer 320 of the present invention. As shown in FIGS. 9A through 9D, the portable spectrometer 320 comprises an enclosure 310 for the optical system (e.g, the light source, dispersive system and detector) of the portable spectrometer 320. The portable spectrometer 320 further comprises a handle 312 by which a user may grasp the portable spectrometer 320. As shown in FIGS. 9A through 9D, the handle 312 comprises a "pistol-grip" shaped handle that a user may grasp while holding the portable spectrometer 320. An activation element 314 (e.g., a trigger, switch, button or the like) may also be used on a portable spectrometer to activate the portable spectrometer to acquire a Raman spectrum of a sample. The portable spectrometer 320 also comprises an output module 332 containing optics for delivering an excitation radiation incident beam to a sample and collecting Raman scattered light from the sample. Such a portable spectrometer 320 may be used in a "point and shoot" manner in which a terminal end 333 of the output module is placed in close proximity to (e.g., touching) a sample material and a user presses a trigger activation element 314 to take a Raman spectrum of the sample. In this embodiment, for example, the output module 332 may comprise an output focusing lens slightly recessed from the terminal end 333 of the output module 332 such that the focal point of the output focusing lens is in close proximity to the terminal end 333 of the output module.

As discussed above, the portable spectrometer may comprise one or more removable output modules 332 that may be interchanged on the portable spectrometer depending on the application. For example, different output modules 332 may be used depending on the form of the sample (e.g., solid, liquid or gas), the location of the sample, or the amount of the sample. The output module 332 may comprise a lens to focus the incident beam on the sample or may deliver collimated light to another optical system (e.g., a microscope, telescope, camera lens or the like) for focusing on the sample. Where the output module 332 is removable from the portable spectrometer 320, for example, the portable spectrometer 320 may further comprise an interlock system for shutting off the light source or blocking the excitation radiation from exiting the spectrometer 320. The interlock, for example, may comprise an electrical an/or mechanical switch that detects the presence of an output module 332 and only activates the light source if an output module 332 is attached to the spectrometer 320.

FIG. 10 further shows a system 410 comprising a portable spectrometer 420 used in combination with a microscope 430. In this embodiment, for example, the output module 432 of the portable spectrometer 420 delivers collimated light to the microscope 430 (i.e., the output module does not comprise an output focusing lens). The collimated incident beam of excitation radiation enters the optical system of the microscope 430, where it is focused onto a sample 435. Raman scattered light is collected by the optical system of the microscope 430 and is returned to the portable spectrometer 420 as collimated light to the output module 432 of the portable spectrometer 420. In the embodiment shown in FIG. 10, the system 410 comprises a communication link 445 for communicating with a device 450, such as computer, PDA or the like. The communication link 445 may comprises a wireless or wired communication link. Via the communication link 445, the device 450 may control the operation of the portable spectrometer 420. The system 410 may optionally further comprise a camera 440 (e.g., video or still picture camera) for monitoring the sample 435, such as during a laser illumination of the sample 435. The camera 440 may also communicate via the communication link 445 with the device 450 and/or the portable spectrometer 420. Thus, a user may monitor the sample 438 via the camera 440 and control the operation of the portable spectrometer 420 remotely. Where the sample 435 comprises a potentially hazardous substance, for example, a user may monitor the operation remotely so as to avoid being exposed to the sample 435. A user may also monitor the operation of the portable spectrometer 420 remotely over a network to which the communication link 445 connects the portable spectrometer 420 and/or the camera 440.

FIG. 11 shows a system 510 in which a Raman spectrum of a sample is taken in a first location 515 via a portable spectrometer 520. The operation may be monitored, recorded and/or controlled in a second location remote from the first location by a device 550. The device 550, for example, may comprise an external computer, a PDA or the like. The system 510 comprises a communication link 545 (wireless or wired) via which the portable spectrometer 520 may communicate with the device 550.

Thus, one or more portable spectrometers 520 may be used in remote locations by a technician (e.g., a police officer or a field agent) that need only be trained in how to properly operate the spectrometer 520, but need not be trained in how to interpret the results of the Raman spectrum obtained. The technician may use the portable spectrometer to collect a Raman spectrum for a sample 535. The portable spectrometer 520 may transmit the results of the spectrum taken for the sample to a remote device via the communication link 545. The result transmitted may comprise data collected or a result of the Raman spectrum reading (e.g., if the control electronics of the portable spectrometer 520 comprises a look up table in data storage that allows for classification of the sampled spectrum at the portable spectrometer 520).

Figure 12:
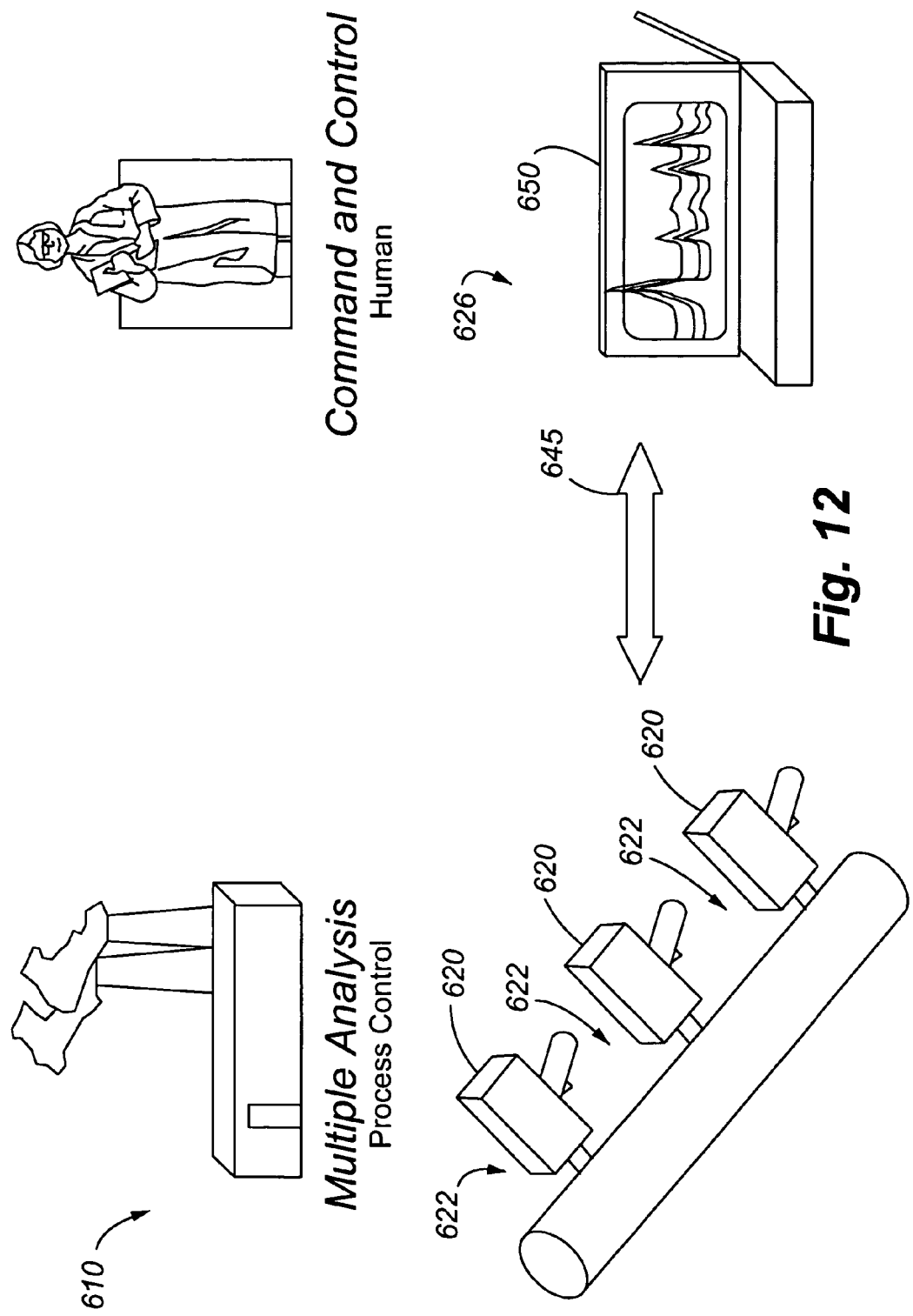
FIG. 12 shows a diagram of an embodiment of an embodiment of a system for remote Raman analysis comprising a plurality of an embodiment of portable Raman spectrometers.

As shown in FIG. 12, a system 610 in accordance with another embodiment of the present invention comprises a plurality of spectrometers 620 located at a plurality of locations 622 for monitoring conditions at the plurality of locations 622. One or more communication link(s) 645 allow the spectrometers 620 to communicate with a remote device 650, such as a computer, PDA or the like. The plurality of spectrometers 620 may, for example, monitor the progress of a chemical process at a plurality of spatially distinct sites, monitor for the presence of chemicals or substances, such as toxic industrial chemicals or substances or banned components such as used in weapons of mass destruction, at one or more location(s) 622. The spectrometers 620 may transmit collected data and/or a result of a Raman spectrum reading as described above.

The collected data or the result received by the device 650 may be analyzed and/or stored by the device 650 or by a user of the device 650 at a remote location 626. Where a plurality of spectrometers 620 are used, for example in the systems shown in FIGS. 11 and 12, the systems allow for the data to be analyzed and/or stored at one or more central location(s) for analysis by a user trained in interpreting Raman spectra information. The device or a user located at the remote location may also control the operation of the spectrometers remotely or issue instructions to the technicians operating the portable spectrometers.

The portable spectrometer may transmit data collected or results obtained from the collected data in real-time and/or may store the collected data and/or results obtained for transmission at a later time. The portable spectrometer, for example, may comprise a data storage element, such as a memory, disk or tape drive, memory stick or the like, for storing data collected and/or results obtained until they are to be transmitted to the device via the communication link.

FIG. 13 shows a system 710 comprising a portable spectrometer 720 and a robot 730 for manipulating the portable spectrometer 720. The portable spectrometer 720 and the robot 730 communicate with a device 750 such as a computer, PDA or the like via one or more communication link(s) 745. The one or more communication link(s) 745 may comprise a wireless link and/or a wired link. The device 750 or a user of the device 750 may control and/or monitor the operation of the portable spectrometer 720 and/or the robot 730 via the one or more communication link(s) 745. In one embodiment, the portable spectrometer 720 and/or the robot 730 may further comprise a camera, video or still, to assist the device 750 or a user of the device 750 in controlling and/or monitoring the operation of the portable spectrometer 720 and/or the robot 730. As described above, where the sample to be tested is hazardous or is located in a hazardous environment, the communication link 745 of the portable spectrometer 720 allows a user to control and/or monitor the portable spectrometer 720 and/or the robot 730 from a safer, remote location.

Figure 14:
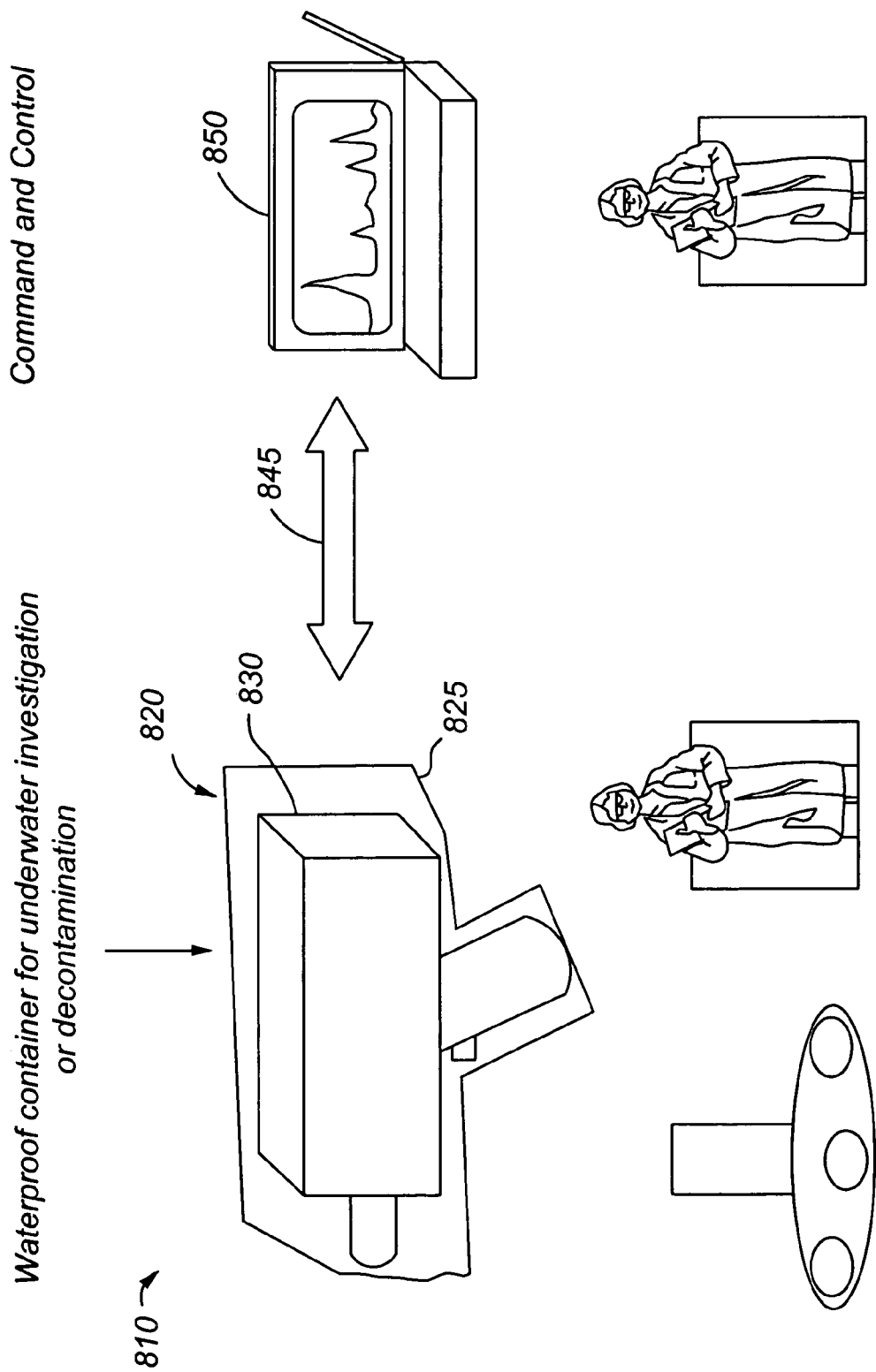
FIG. 14 shows a diagram of an embodiment of an embodiment of a system for remote Raman analysis comprising an embodiment of a portable Raman spectrometer adapted for use in a harmful environment.

FIG. 14 shows yet another embodiment of a spectrometer 820 and a system 810 including the spectrometer 820 in accordance with the present invention. The embodiment of the spectrometer 820 shown in FIG. 14 comprises a protective container 825 or housing 830 for the spectrometer 820. In one embodiment, the protective container 825 may comprise an additional housing into which the spectrometer 820 may be placed when the spectrometer 820 is to be used or otherwise exposed to an environment that may be harmful to the spectrometer 820 under normal conditions. Alternatively, the housing 830 of the spectrometer 830 itself may be constructed as a protective container for protecting the components of the spectrometer 820 from an abnormally destructive environment.

In one embodiment, for example, the protective container 825 or housing 830 may comprise a waterproof or water-resistant container or housing in which the spectrometer 820 be used in an underwater or high humidity environment. For example, a protective container may comprise a waterproof container 825 similar to a water-proof container currently used for cameras to take photographs underwater while diving or snorkeling. Alternatively, as with certain underwater cameras, the housing 830 of the spectrometer itself may comprise a waterproof or water-resistant casing protecting the components of the spectrometer. In this embodiment, for example, a portable spectrometer 820 may be used in an underwater environment by a diver or a robotic submersible to collect a Raman spectrum of a sample located in an underwater environment.

While one potentially harmful environment to a spectrometer 820 comprises an underwater environment, the protective container 825 or housing 830 may also be designed to protect the spectrometer 820 from other harmful environments, such as corrosive or other damaging chemical environments, high electromagnetic fields (e.g., shielding) or environments in which static electricity is a concern (e.g., grounding or insulating).

As described above, the spectrometer 820 may be equipped with a communication port for communicating with an external device 850 over a communication link 845 (a wireless link and/or a wired link).

Figure 15:
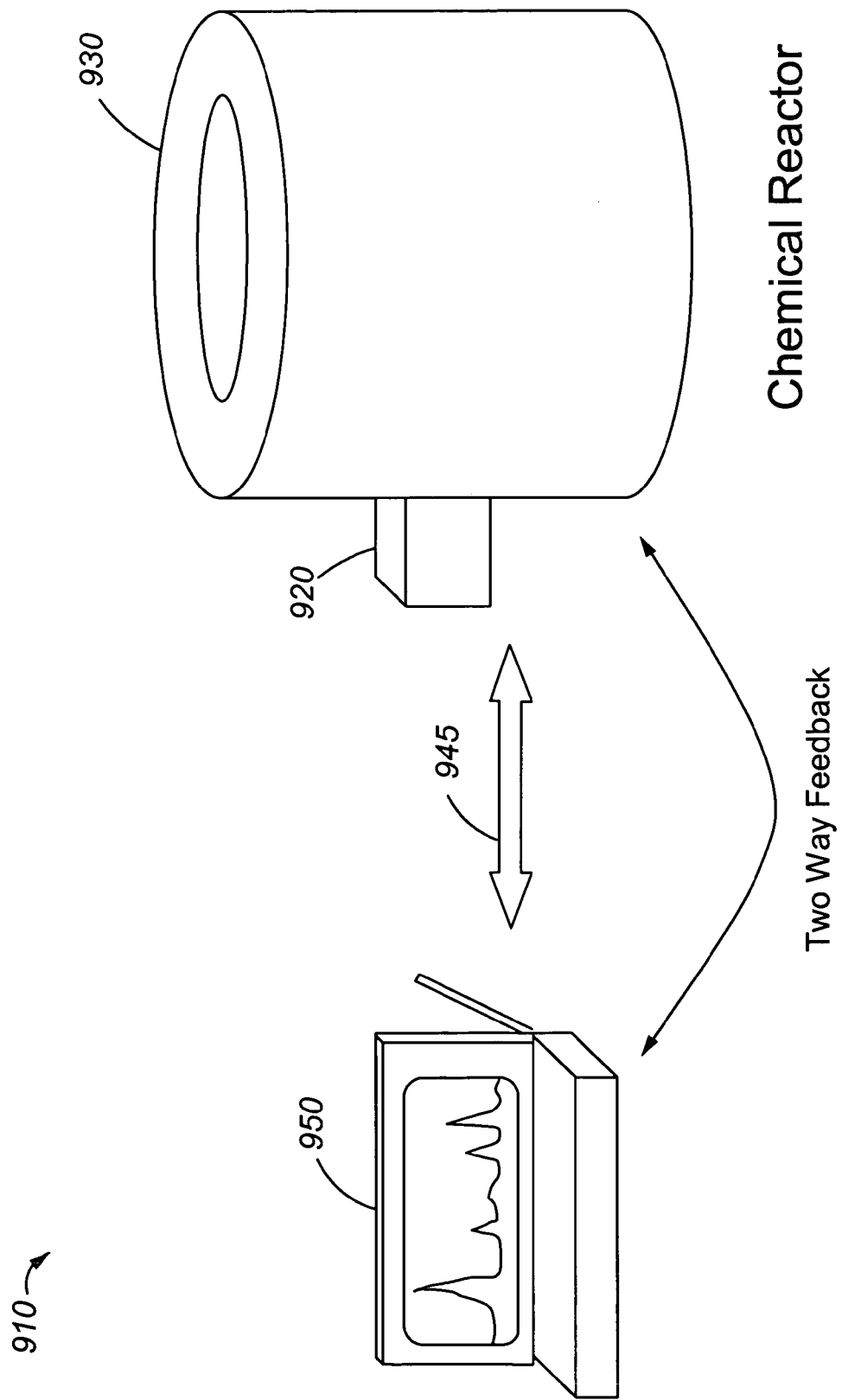
FIG. 15 shows a diagram of an embodiment of a system for monitoring a chemical reaction comprising an embodiment of a Raman spectrometer.

FIG. 15 shows another embodiment of a system 910 in accordance with the present invention. The system 910 may comprise a spectrometer 920 for use in monitoring a chemical reaction taking place, such as in a chemical reactor 930. In one embodiment, an output module of the spectrometer 920, for example, may comprise a collimated beam tube or a fiber optic waveguide that extends to a location in which the chemical reaction is taking place (e.g., with a chemical reactor 930). In another embodiment, the spectrometer 920 may be integrated with the chemical reactor 930. The spectrometer 920 may further communicate with an external device 950, such as through a communication link 945. The communication link 945 may comprise a single-direction is or dual-direction link that comprises one or more wireless and/or wired link. The spectrometer 920 may transmit data collected from the reaction and/or may transmit results obtained from the collected data to the external device 950 via the communication link 945. The external device 950 and/or a user monitoring the external device 950 may monitor the process of the chemical reaction via the collected data or results obtained from the collected data. The external device 950 and/or a user monitoring external device may further adjust parameters associated with the chemical reaction through feedback directed to the chemical reactor 930.

Figure 16:
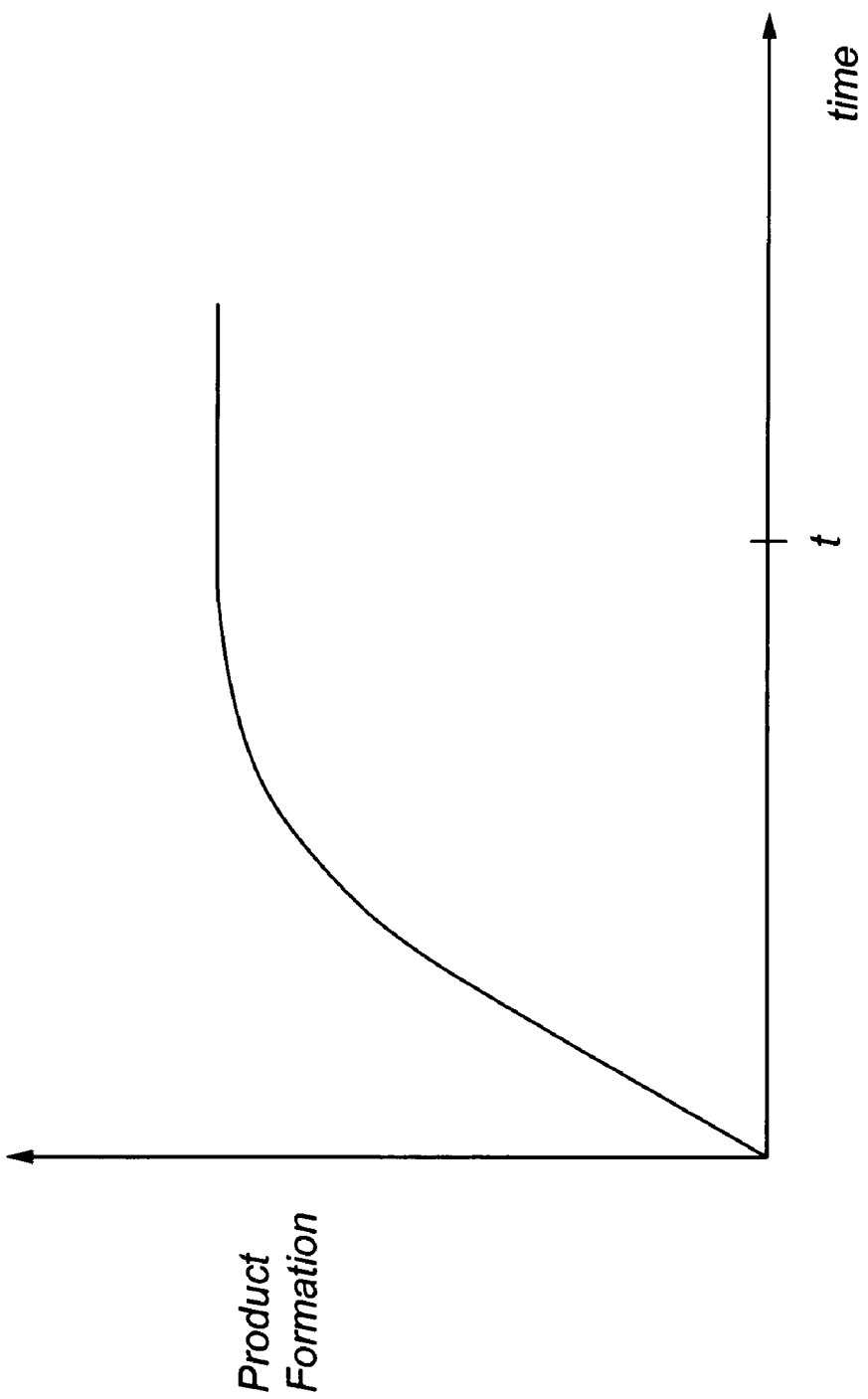
FIG. 16 shows a graphical representation of an exemplary product formulation created via a chemical reaction.

FIG. 16, for example, shows a graph of an amount of a product formulation created by a chemical reaction on a vertical axis plotted versus time on the horizontal axis. As shown in FIG. 16, the amount of product formulation created by the chemical reaction increases in a generally linear relationship with respect to time in which the amount product formulation created plateaus after a time period t indicating that the chemical reaction is complete. Thus, by monitoring the amount of product formulation present in a reaction chamber 930, the spectrometer 920 and/or the external device 950 can determine when the chemical reaction is complete when the slope of the product formulation created versus time plateaus after time t.

As described above, a plurality of spectrometers 920 may be used to monitor a plurality of chemical reactions and may transmit the data collected by the spectrometer and/or a result obtained from the collected data to the external device 950. In this embodiment, for example, one or more external device(s) and or a user of the one or more external device(s) may be used to monitor a plurality of chemical reactions progressing at the same time.

Although the present invention has been described in conjunction with its preferred embodiments, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. A spectrometer for obtaining Raman spectrum information from a sample, the spectrometer comprising:
 a light source for providing an excitation radiation;
 a detector for detecting Raman scattered light;
 an optical system for directing said excitation radiation toward the sample, receiving Raman scattered light from the sample, and providing the Raman scattered light to said detector,
 wherein said optical system comprises a collimated beam tube for transmitting said excitation radiation in the form of a collimated light signal on-axis to the sample via an external optical system.

2. The spectrometer of claim 1, wherein said external optical system comprises at least one of a microscope, a telescope and a camera lens.

3. The spectrometer of claim 1, wherein the spectrometer is adapted to couple to a microscope to provide microscopic Raman spectroscopy analysis.

4. The spectrometer of claim 1, wherein a microscopic Raman spectroscopy system comprises the spectrometer coupled to a microscope.

5. The spectrometer of claim 1, wherein the spectrometer is adapted to couple to the external optical system to provide remote Raman spectroscopy analysis.

6. The spectrometer of claim 1, wherein a remote Raman spectroscopy system comprises the spectrometer coupled to a telescope.

7. The spectrometer of claim 1, wherein said collimated beam tube comprises a quartz material.

8. The spectrometer of claim 7, wherein said collimated beam tube comprises a quartz tube.

9. The spectrometer of claim 1, wherein said collimated beam tube comprises an output module.

10. The spectrometer of claim 9, wherein said output module comprises a releasably engageable output module.

11. The spectrometer of claim 1, wherein said light source comprises a diode laser.

12. The spectrometer of claim 11, wherein said diode laser comprises a near-infrared (NIR) wavelength diode laser.

13. The spectrometer of claim 11, wherein said diode laser comprises an infrared (IR) wavelength diode laser.

14. The spectrometer of claim 13, wherein said detector comprises an InGaAs detector.

15. The spectrometer of claim 1, wherein said detector comprises an InGaAs detector.

16. An integrated Raman spectrometer for obtaining Raman spectrum information from a sample, the integrated Raman spectrometer comprising:
a plate having a mounting surface;
a light source module for providing an excitation radiation, the light source module mounted to said mounting surface of said plate;
a detector module for detecting Raman scattered light mounted to said mounting surface of said plate;
an optical system adapted to direct said excitation radiation toward the sample, receive Raman scattered light from the sample, and provide the Raman scattered light to said detector module, said optical system mounted to said mounting surface of said plate, and
a collimated beam tube for transmitting said excitation radiation from said optical system toward the sample in the form of a collimated light signal.

17. The integrated Raman spectrometer of claim 16, wherein said plate comprises a base plate.

18. The integrated Raman spectrometer of claim 16, further comprising a control electronics for controlling an operation of the integrated Raman spectrometer.

19. The integrated Raman spectrometer of claim 18, wherein said control electronics is mounted on a single board that is mounted to said plate.

20. The integrated Raman spectrometer of claim 18, further comprising a power supply for powering said control electronics.

21. The integrated Raman spectrometer of claim 20, wherein said power supply is adapted to receive a battery to power said control electronics.

22. The integrated Raman spectrometer of claim 20, wherein said power supply is adapted to receive alternating current power.

23. The integrated Raman spectrometer of claim 16, wherein said optical system comprises an adjustable diffraction grating for dividing the Raman scattered light into spatial separated wavelengths and for directing said spatial separated wavelengths toward said detector module.

24. The integrated Raman spectrometer of claim 23, wherein said adjustable diffraction grating comprises a diffraction surface fixed to a rocker.

25. The integrated Raman spectrometer of claim 24, wherein said rocker is adjustable to target the spatial separated wavelengths vertically at said detector module.

26. The integrated Raman spectrometer of claim 16 further comprising an output port for communicating with an external device.

27. The integrated Raman spectrometer of claim 16, wherein said output port comprises an antenna for wirelessly communicating with an external device.

28. The integrated Raman spectrometer of claim 27, wherein said output port is adapted for wireless communication with an external device using at least one of a Bluetooth communication, an IEEE 802.11a communication, an IEEE 802.11b communication, an IEEE 802.11g communication, an infrared communication, and an IrDA communication.

29. The integrated Raman spectrometer of claim 27, wherein said output port comprises at least one of a parallel port, a serial port, a universal serial port, an IEEE 1394 port, a FireWire (™) port, an Ethernet port, a modem port, and a cable modem port.

30. The integrated Raman spectrometer of claim 16, wherein said light source comprises a diode laser.

31. The integrated Raman spectrometer of claim 30, wherein said diode laser comprises a near-infrared (NIR) wavelength diode laser.

32. The integrated Raman spectrometer of claim 30, wherein said diode laser comprises an infrared (IR) wavelength diode laser.

33. The integrated Raman spectrometer of claim 32, wherein said detector comprises an InGaAs detector.

34. The integrated Raman spectrometer of claim 16, further comprising a protective container for protecting the portable spectrometer from a harmful environment.

35. The integrated Raman spectrometer of claim 34, wherein said protective container comprises a waterproof container for protecting the portable spectrometer underwater.

36. The integrated Raman spectrometer of claim 16, wherein said housing comprises a protective housing for protecting the portable spectrometer from a harmful environment.

37. The integrated Raman spectrometer of claim 36, wherein said housing comprises a waterproof housing for protecting the portable spectrometer underwater.

38. A portable spectrometer for obtaining Raman spectrum information from a sample, the portable spectrometer comprising:
a housing comprising a handle and an activation switch;
a light source mounted within said housing for providing an excitation radiation;
a detector mounted within said housing for detecting Raman scattered light; and
an optical system for directing said excitation radiation toward the sample external to said housing, receiving Raman scattered light from the sample, and providing the Raman scattered light to said detector,
wherein said optical system comprises a collimated beam tube for transmitting said excitation radiation in the form of a collimated light signal.

39. The portable spectrometer of claim 38, wherein said optical system comprises an output module attached to said housing for directing said excitation radiation to the sample and for receiving the Raman scattered light from the sample.

40. The portable spectrometer of claim 39, wherein said output module is releasably attachable to said housing.

41. The portable spectrometer of claim 39, wherein said output module comprises a terminal end and an output focusing lens that focuses said excitation radiation at about said terminal end.

42. The portable spectrometer of claim 38, further comprising a power supply for powering said control electronics.

43. The portable spectrometer of claim 42, wherein said power supply is adapted to receive a battery to power said control electronics.

44. The portable spectrometer of claim 42, wherein said power supply is adapted to receive alternating current power.

45. The portable spectrometer of claim 38 further comprising an output port for communicating with an external device.

46. The portable spectrometer of claim 45, wherein said output port comprises an antenna for wirelessly communicating with an external device.

47. The portable spectrometer of claim 45, wherein said output port is adapted for wireless communication with an external device using at least one of a Bluetooth communication, an IEEE 802.11a communication, an IEEE 802.11b communication, an IEEE 802.11g communication, an infrared communication, and an IrDA communication.

48. The portable spectrometer of claim 45, wherein said output port comprises at least one of a parallel port, a serial port, a universal serial port, an IEEE 1394 port, a FireWire (™) port, an Ethernet port, a modem port, and a cable modem port.

49. The portable spectrometer of claim 38, wherein said light source comprises a diode laser.

50. The portable spectrometer of claim 49, wherein said diode laser comprises a near-infrared (NIR) wavelength diode laser.

51. The portable spectrometer of claim 49, wherein said diode laser comprises an infrared (IR) wavelength diode laser.

52. The portable spectrometer of claim 51, wherein said detector comprises an InGaAs detector.

53. The portable spectrometer of claim 38, further comprising a protective container for protecting the portable spectrometer from a harmful environment.

54. The portable spectrometer of claim 53, wherein said protective container comprises a waterproof container for protecting the portable spectrometer underwater.

55. The portable spectrometer of claim 38, wherein said housing comprises a protective housing for protecting the portable spectrometer from a harmful environment.

56. The portable spectrometer of claim 55, wherein said housing comprises a waterproof housing for protecting the portable spectrometer underwater.

57. The spectrometer of claim 38, wherein said detector comprises an InGaAs detector.

58. A chemical reactor having a built-in Raman spectrometer for monitoring a chemical reaction, the chemical reactor comprising:
    a reaction chamber for providing a chemical reaction; and
    a Raman spectrometer built-in to the reactor for monitoring a chemical reaction in said reaction chamber, the Raman spectrometer comprising:
        a light source for providing an excitation radiation,
        a detector for detecting Raman scattered light, and
        an optical system for directing said excitation radiation toward said reaction chamber, receiving Raman scattered light from said reaction chamber, and providing the Raman scattered light to said detector,
        wherein said optical system comprises a collimated beam tube for transmitting said excitation radiation in the form of a collimated light signal.

59. The chemical reactor of claim 58, wherein said Raman spectrometer monitors an amount of a product formed in said reaction chamber.

60. The chemical reactor of claim 59, wherein the reactor indicates that a reaction is complete based upon said amount of a product formed in said reaction chamber.

61. The chemical reactor of claim 59, wherein the reactor indicates that the reaction is complete when said amount of a product formed in said reaction chamber substantially plateaus.

62. A method for receiving a Raman spectrum of a sample, the method comprising:
    providing a Raman spectrometer comprising:
        a light source for providing an excitation radiation,
        a detector for detecting Raman scattered light, and
        an optical system comprising a collimated beam tube, wherein the excitation radiation is directed on-axis to the sample via the collimated beam tube;
    receiving Raman scattered light from the sample, and
    providing the Raman scattered light to said detector via the collimated beam tube.

63. The method of claim 62, wherein the excitation radiation is provided to the sample via the collimated beam tube and an external optical system.

64. The method of claim 63, wherein the external optical system comprises at least one of a microscope, a telescope, and a camera lens.

65. The method of claim 63, wherein the Raman spectrometer is adapted to couple to a microscope to provide microscopic Raman spectroscopy analysis.

66. The method of claim 63, wherein the Raman spectrometer is adapted to couple to the external optical system to provide remote Raman spectroscopy analysis.

67. The method of claim 62, wherein Raman spectrometer comprises an integrated Raman spectrometer comprising a plate having a mounting surface, wherein the light source comprises a light source module mounted to the mounting surface of the plate and the detector comprises a detector module mounted to the mounting surface of the plate.

68. The method of claim 62, wherein the Raman spectrometer comprises a portable Raman spectrometer comprising a housing and a switch, wherein the light source and the detector are mounted within the housing.

69. The method of claim 62, further comprising providing a chemical reaction within a chemical reactor and monitoring the chemical reaction within the chemical reactor via the Raman spectrometer.

70. A spectrometer for obtaining Raman spectrum information from a sample, the spectrometer comprising:
    a light source for providing an excitation radiation;
    a detector for detecting Raman scattered light;
    an optical system for directing said excitation radiation toward the sample, receiving Raman scattered light from the sample, and providing the Raman scattered light to said detector,
    wherein said optical system comprises a collimated beam tube for transmitting said excitation radiation in the form of a collimated light signal on-axis to the sample via a lens.

* * * * *